US009745588B2

(12) United States Patent
Striedner et al.

(10) Patent No.: US 9,745,588 B2
(45) Date of Patent: Aug. 29, 2017

(54) TRANSCRIPTION TERMINATOR SEQUENCES

(75) Inventors: Gerald Striedner, Vienna (AT); Alexander Wittwer, Vienna (AT)

(73) Assignees: SANDOZ AG, Basel (CH); BOEHRINGER INGELHEIM RCV GMBH & CO KG, Vienna (AT)

( * ) Notice: Subject to any disclaimer, the term of this patent is extended or adjusted under 35 U.S.C. 154(b) by 0 days.

(21) Appl. No.: 13/487,083

(22) Filed: Jun. 1, 2012

(65) Prior Publication Data

US 2013/0059344 A1 Mar. 7, 2013

(30) Foreign Application Priority Data

Jun. 3, 2011 (EP) .................... 11168637

(51) Int. Cl.
| | | |
|---|---|---|
| C12N 15/63 | (2006.01) | |
| C12N 15/70 | (2006.01) | |
| C12N 1/00 | (2006.01) | |
| C12N 5/00 | (2006.01) | |
| C12N 5/10 | (2006.01) | |
| C12N 15/67 | (2006.01) | |
| C12N 15/79 | (2006.01) | |
| C07H 21/04 | (2006.01) | |

(52) U.S. Cl.
CPC ............. *C12N 15/63* (2013.01); *C12N 15/70* (2013.01)

(58) Field of Classification Search
None
See application file for complete search history.

(56) References Cited

FOREIGN PATENT DOCUMENTS

| JP | 2009-523428 A | 6/2009 |
|---|---|---|
| WO | WO 2007/087478 A2 | 8/2007 |

OTHER PUBLICATIONS

Sohn et al., "Sequential multiple functions of the conserved sequence in sequence-specific termination by T7 polymerase" 102(1) Proceedings of the National Academy of Sciences 75-80 (2005).*
Wu et al., "Transcription termination: Nucleotide sequence at 3' end of tryptophan operon in *Esherichia coli*" 75(11) Proceedings of the National Academy of Sciences 5442-5446 (1978).*
Wu et al., "Tandem termination sites in the tryptophan operon of *Escherichia coli*" 78(5) Proceedings of the National Academy of Sciences 2913-2917 (1981).*
Meyerhof et al., "Transcription termination and processing of transcripts from tRNA-related Xenopus satellite DNA sequences" 164 European Journal of Biochemistry 287-283 (1987).*
Lyakhov et al., "Pausing and Termination by Bacteriophage T7 RNA Polymerase" 280 Journal of Molecular Biology 201-213 (1998).*
Database NCBI [Online], Apr. 27, 2010, "*Escherichia coli* APEC 01 Plasmid pAPEC-01-ColBM, complete sequence," XP002661815, retrieved from NCBI Database accession No. NC_009837.1.
"WebGeSTer: Analysis of NC_009837," XP002661816, Retrieved from the Internet: URL:http://pallab.serc.iisc.ernet.in/gester/genome_view.php?start=1&end=100000&cds=&dir_code=62736339&Submit=Submit [retrieved on Oct. 19, 2011].
Database NCBI [Online], May 30, 2010, "*Escherichla coli* APEC 01, complete genome," XP002661817, retrieved from NCBI Database accession No. NC_008563.1.
"WebGeSTer: Analysis of NC_005863," XP002661818, Retrieved from the Internet: URL:http://pallab.serc.iisc.ernet.in/gester/genome_view.php?start=300000&end=400000&cds=&dir_code=25407231&Submit=Submit [retrieved on Oct. 19, 2011].
"Artificial transcriptional terminators," Sep. 5, 2006, XP55025199, Retrieved from the Internet: URL:http://openwetware.org/wiki/Artificial_transcriptional_terminators [retrieved on Apr. 20, 2012].
Carafa et al., "Prediction of rho-independent *Escherichia coli* transcription terminators," Journal of Molecular Biology, Academic Press, United Kingdom, vol. 216, No. 4, Dec. 20, 1999, pp. 835-858, XP005593304.
A. Mitra et al., "WebGeSTer DB—a transcription terminator database," Nucleic Acids Research, vol. 39, No. Database, Oct. 23, 2010, pp. D129-D135, XP55008809.
S. Unniraman,"Conserved economics of transcription termination in eubacteria" Nucleic Acids Research, vol. 30, No. 3, Feb. 1, 2002, pp. 675-684, XP55008793.
Quiagen, "The QIAexpressionist: A handbook for high-level expression and purification of 6xHis-tagged proteins," Jun. 2003, XP002661819, Retrieved from the Internet; URL:http://www.qiagen.com/literature/handbooks/literature.aspx?id=1000182.
S. Unniraman, "Alternate paradigm for Intrinsic transcription termination in eubacteria," Journal of Biological Chemistry, vol. 276, No. 45, Nov. 2, 2001, pp. 41850-41855, XP55008064.
D. I. Friedman et al., "RNA 3' end formation in the control of gene expression," Annual Review of Genetics, vol. 21, No. 1, Dec. 1, 1987, pp. 453-488, XP55008811.
E. A. Lesnik, "Prediction of rho-independent transcriptional terminators in *Escherichia coli*," Nucleic Acids Research, vol. 29, No. 17, Sep. 1, 2001, pp. 3583-3594, XP55023605.
K. S. Wilson, "Transcription Termination at Intrinsic Terminators: The Role of the RNA Hairpin," Proceedings of the National Academy of Sciences, vol. 92, No. 19, Sep. 12, 1995, pp. 8793-8797, XP55023604.
Austin Che, "Part:BBa B0017—parts.igem.org", Jan. 8, 2004, XP055166902, 2 pages.
Chung Nan Chang et al., "Nucleotide sequence of the alkaline phosphatase gene of *Escherichia coli*", Gene, Elsevier, Amsterdam, NL, vol. 44, No. 1, Jan. 1, 1986, pp. 121-125, XP025687772.
Examination Report issued on Feb. 10, 2015 in European Application No. 12727349.8.

(Continued)

*Primary Examiner* — Nancy J Leith
(74) *Attorney, Agent, or Firm* — Birch, Stewart, Kolasch & Birch, LLP

(57) ABSTRACT

The present invention provides new transcription termination signal sequences, especially a polynucleotide comprising at least two consecutive transcription termination signals, characterized in that consecutive transcription termination signals comprise at least a first and a second transcription termination signal that are at most 1000 nucleotides apart, and at least one of the termination signal has or encodes a RNA hairpin structure.

55 Claims, 10 Drawing Sheets

(56) References Cited

OTHER PUBLICATIONS

Reshma Shetty, "Part:BBa B0014 Double Terminator (B0012-B0011)", Jul. 16, 2003, XP055167106, 2 pages.
Reshma Shetty, "Part:BBa B0015 Double Terminator (B0010-B0012)", Jul. 17, 2013, XP0551671 04, 2 pages.
He et al., Characterization of an Unusual, Sequence-specific Termination Signal for T7 RNA Polymerase, The Journal of Biological Chemistry, 1998, pp. 18802-18811, vol. 273, No. 30.
Japanese Office Action and Translation for JP 2014-513216 dated Mar. 29, 2016.
Mitra et al., Occurrence, divergence and evolution of intrinsic terminators across Eubacteria, Genomics (2009), pp. 110-116, vol. 94 and Supplementary Figure 1.

\* cited by examiner

Continuation of Fig. 1:

A: pTZENIT

B: pET30a

A: pTZENIT

B: pET30a

A: pTZEMIT

B: pET30a

TRANSCRIPTION TERMINATOR SEQUENCES

This Nonprovisional application claims priority Under 35 U.S.C. §119 on European Patent Application No. 11168637.4 which has a filing date of Jun. 3, 2011.

The present invention relates to the field of expression systems and polynucleotide constructs.

For a sufficient yield of recombinant protein produced by an expression system one has to consider several aspects when designing polynucleotide constructs and the recombinant expression system. Important aspects are the type of host cell culture and the selection of an appropriate transfection system that guarantees cell viability during the entire production process and high expression efficiency. Often these concerns are antagonistic since a high expression rate (of secondary proteins unnecessary for survival) is detrimental to cell health and survival. A controllable expression system is desired that allows the specific adjustment of expression rate and of modifications to the cell metabolism. One important aspect of recombinant expression systems is transcriptional efficiency, including efficiency of termination. Low termination efficiency leads to read-through transcription and the production of lengthy mRNAs that by themselves are stressful to a cell, but even more so can lead to the expression of unwanted proteins or disturb the replication control of the transgene construct—in particular in the field of plasmid vectors. Unwanted replication in turn produces many copy numbers of the transgene, thereby elevating the metabolic burden on the cellular system, which multiplies the problem of inefficient expression systems.

Transcription lies at the heart of cellular gene expression, and thus may present the most powerful option to manipulate the expression rate of a single gene or group of genes. Once the ternary complex is build up, it must be stable enough to allow the incorporation of up to hundred bases per second without dissociation of the RNA polymerase during non terminating transcriptional pauses or delays. Thus a tight connection of the elongating RNA polymerase with the template DNA and the producing RNA transcript is essential for the ability to produce mRNAs with a length of several hundred or thousand nucleotides.

After transcriptional initiation and the building up of an extraordinary stable ternary complex the enzyme moves along the template, incorporates nucleotides one by one and produces the desired RNA chain. The synthesis of RNA and the release of the mRNA of a single gene or transcriptional operon have to be stopped at distinct sites on the template. This process is called transcriptional termination and resembles the events during transcriptional initiation but in reversed order, resulting in the dissociation of RNA polymerase and the release of transcribed RNA. Termination occurs in response to well defined signals within the template DNA, the so called transcriptional terminators. Like every biological process even termination is not a make or break decision, therefore does not happen in an extent of 100%. Indeed terminators vary widely in their efficiencies of termination, with great differences in termination efficiency (TE). Indeed, termination signals are highly specific for a given RNA polymerase. A non-terminating event is also described as read through of the polymerase.

Terminators can be classified into several groups. At the first group of termination signals the core enzyme can terminate in vitro at certain sites in the absence of any other factors (as tested in vitro). These sites of termination are called intrinsic terminators or also class I terminators. Intrinsic terminators usually share one common structural feature, the so called hairpin or stem-loop structure. On the one hand the hairpin comprises a stem structure, encoded by a dG-dC rich sequence of dyad symmetrical structure. On the other hand the terminator also exhibits a dA-dT rich region at the 3'-end directly following the stem structure. The uridine rich region at the 3' end is thought to facilitate transcript release when RNA polymerase pauses at hairpin structures.

For a long time the stability of the hairpin mediated by G-C pairs within the stem structure was believed to be the most essential compartment of the hairpin structure to affect TE. Insertion of putative bases into the stem structure should theoretically result in a higher overall $\Delta G$ value, and therefore the overall TE should increase. Surprisingly the increase of thermodynamic stability by inserting G-C pairs did not result in higher TE, indicating that the stability of the hairpin structure is not the only essential determinant of termination. It is assumed that in addition to stability the three dimensional structure of the hairpin plays an important role in termination. For the most characterized intrinsic terminators the distance from the first closing base pair of the stem structure to the first termination position is conserved. That invariance could be seen as a putative evidence for the importance of the three dimensional structure. As a conclusion it seems that the hairpin has to assume a distinct three dimensional shape, in order to interact with the elongating polymerase.

Wilson and von Hippel (PNAS 92, 1995; 8793-8797) describe variants of the tR2 hairpin terminator and termination efficiency by the E. coli RNA polymerase. Optimal hairpin structures for maximal termination efficiency had a stem of 8 or 9 mostly G/C base pairs and a loop of 4-8 residues followed by 6-8 rU residues. Further lengthening the stem reduced termination efficiency.

Orosz et al. (Eur. J. Biochem 201, 1991: 653-659) investigated structural requirements of the E. coli terminator of the rrnB gene by the E. coli RNA polymerase. The native terminator region consists of two hairpin terminators with two intermittent small repeats that are thought to be capable to form small stems each. Interestingly, deletion of all structures except the first terminator did not result in a reduction of termination efficiency. The stem of this first terminator had a G/C content of 43%.

Jeng et al. (J Biol Chem 267 (27), 1992: 19306-19312) describe in vitro termination of the thr attenuator by the bacteriophage T7 RNA polymerase. Termination of the thr attenuator is potentially influenced by remote sequences upstream and distal of the thr attenuator, a G/C rich stem-loop hairpin of 7 G/C basepairs with variable A/T additions, a deoxythymidine stretch preceding the hairpin, and the loop structure (the inverse sequence of the thr attenuator being favoured). Later investigations showed that an adenine residue stretch upstream of the stem-loop is not required for termination (Yang et al., J Biol Chem 270(49), 1995: 23330-23336).

Terminators are contained in bacterial sequences such as in plasmid pAPEC-O1-ColBM (NCBI database acc. no. NC_009837.1) or the genome of E. Coli APEC O1 strain (NCBI database acc. no. NC_008563.1).

Carafa et al. (J Mol Biol 216(4) (1999): 835-858) describe Rho-independent E. Coli transcription terminators.

Mitra et al. (Nucleic Acids Research, 39 (2011): D129-D135) provide a presentation of the WebGeSTer database, a transcription terminator database.

Unniraman et al. (Nucleic Acids Research 30 (3) (2002): 675-684) provide a review of certain terminator structures and classification.

Quiagen's QIAexpress pQE vector ("The QIAexpress System", The QIAexpressionist 06/2003, 5th ed., page 15) contains two terminators.

Unniraman et al. (Journal of Biological Chemistry, 276 (45) (2001): 41850-41855) relates to intrinsic transcription terminators in eubacteria.

Friedman et al. (Annual Review of Genetics, 21 (1) (1987): 453-488) provide a review on type I and type II terminators.

Lesnik et al. (Nucleic Acid Research, 29(17) (2001): 3583-3594) describe the program RNAMotif for use in searching intrinsic rho-independent terminators.

An objective of the present invention is to provide improved expression systems with increased efficiency for the expression of a desired product by effective transcriptional termination, especially of highly processive RNA polymerases like the T7 RNA polymerase.

This objective is solved by the subject matter of the claims and definitions described herein.

In a first aspect, the present invention provides a polynucleotide comprising at least two consecutive transcription termination signals, wherein said consecutive transcription termination signals comprise at least a first and a second transcription termination signal that are at most 1000 nucleotides apart, and at least one of the termination signal has or encodes a RNA hairpin structure. According to the present invention it has been found that consecutive termination signals can influence on another and lead to a dramatically increased termination efficiency, especially if at least one terminator comprises a hairpin structure. Said hairpin has a structure comprising a stem of at least 12 internal base pairs with at least 60% G or C ("G/C") nucleic acids. In preferred embodiments the hairpin has a special structure as defined in the second aspect. The invention provides polynucleotides comprising combinations of 2, 3, 4 or more termination signals that are operatively linked to allow termination after transcription of a preceding coding sequence in concerted action to increase termination efficiency.

In a second aspect the invention further provides a polynucleotide comprising at least one transcription termination signal comprising a hairpin structure having the sequence Y-U/T-NNG-Z,
wherein Y is a nucleotide sequence of at least 8 nucleotides in length and with a G/C content of at least 60%, preferably at least 70%,
Z is a nucleotide sequence with at least 70% complementarity to Y,
the complementary nucleotides of Z being base paired with the nucleotides of Y, and sequence U/T-NNG being a loop with no base pairing to Y or Z, with N being any nucleotide selected from T(U), A, C, G; preferably the sequence U/T-NNG is U/T-U/T-CG. This second aspect is combinable with the inventive first aspect: This type of terminator can also be used as secondary hairpin on the polynucleotide or may further define the primary hairpin given the limitations of the first aspect are met (Y and Z being at least 12 nucleotides in length). Especially if used as only terminator of a particular gene or expression construct, longer stem structures are preferred, e.g. at least 13, 14, 15, 16 or more base pairs (Y and Z). According to the invention termination efficiency can be increased by further increasing the G/C content, stem complementarity and optimizing the loop, which will be explained in more detail below. All these options increase hairpin stability which leads to increased termination efficiency as has been found according to the present invention. Generally, the formation Gibbs-energy (dG) of the hairpin is lowered by these structural optimizations. However, simple dG optimization does not necessary lead to increased termination efficiency as has been found by Wilson and von Hippel (supra): increasing the stem length beyond 9 base pairs—although it decreases dG (and increases hairpin stability)—did not result in an increase of termination efficiency.

As used herein, a "/" in a nucleotide sequence or nucleotides given in brackets refer to alternative nucleotides, such as alternative U in a RNA sequence instead of T in a DNA sequence. Thus, U/T or U(T) indicate one nucleotide position that can either be U or T. Likewise, A/T refers to nucleotides A or T; G/C refers to nucleotides G or C. Due to the functional identity between U and T any reference to U or T herein shall also be seen as a disclosure as the other one of T or U. E.g. the reference to the sequence UUCG (on a RNA) shall also be understood as a disclosure of the sequence TTCG (on a corresponding DNA). For simplicity only, only one of these options may be described herein.

Complementary nucleotides or bases are those capable of base pairing such as A and T (or U); G and C; G and U.

A hairpin or stem-loop is a RNA structure of a RNA single strand portion which folds onto itself to form (internal) base pairs within the stem and not base pairing in the intermediary loop sequence between the stem portions. The loop is preferably short, e.g. 3, 4, 5, 6, 7 or 8 nucleotides in length. The inventive polynucleotide may have 1, 2, 3, 4 or more hairpins, at least 1, 2, 3 or 4 being as defined herein, with at least one having a larger stem length of at least 12 base pairs, preferably in the range of 14 to 26 base pairs.

The inventive polynucleotide can be DNA (usually encoding the terminator) or RNA (which usually is able to fold into the hairpin structure and may comprise the inventive terminator). The polynucleotide can be single stranded (especially for RNA) or double stranded (especially for DNA).

As used herein, "identity" means the percentage of identical nucleotide at corresponding positions in two or more sequences when the sequences are aligned to maximize sequence matching, i.e., taking into account gaps and insertions. Methods to determine identity are designed to give the largest match between the sequences tested. Moreover, methods to determine identity are codified in publicly available computer programs. Computer program methods to determine identity between two sequences include, but are not limited to, the GCG program package, BLASTP, BLASTN, and FASTA. The BLAST program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity. BLASTN can e.g. be run using default parameters with an open gap penalty of 11.0 and an extended gap penalty of 1.0 and utilizing the blosum-62 matrix.

As used herein, "comprising" shall be understood as referring to an open definition, allowing further members of similar or other features. "Consisting of" shall be understood as a closed definition relating to a limited range of features.

"Termination" as used herein shall refer to transcription termination if not otherwise noted. "Termination signal" or simply "terminator" refers to a "transcription termination signal" if not otherwise noted. Terminators are sequences that hinder or stop transcription of a polymerase. The terminators of the present invention are especially optimized for the T7 RNA polymerase but can also effect termination for other RNA polymerases to some extent.

"ORF" or "Open Reading Frame" is a nucleotide sequence that can be translated into a polypeptide. The coding sequence ("CDS") of such a stretch of sequence is uninterrupted by a stop codon. Stop codons may be present in intros that are excised during gene expression. An ORF that represents the coding sequence for a full protein begins with a "start" codon, usually ATG, and terminates with one of the "stop" codons. For the purposes of this application, an ORF may be any part of a coding sequence, with or without start and/or stop codons. "ORF" and "CDS" may be used interchangeably for a sequence encoding a gene product.

As used herein, the terms "operably linked" or "operably positioned" relative to a ORF, e.g. in an expression cassette, means a sequence having terminator activity of the invention is in a functional relationship with another nucleotide component of the nucleic acid molecule. For example, a terminator is operably linked to a coding sequence if it affects the transcription of the coding sequence. Such an operable linkage can e.g. be by providing the inventive terminator on the same DNA molecule as the coding sequence for a gene. Two or more terminators can be operatively linked if they are positioned to each other to provide concerted termination of a preceding coding sequence. Particular preferred the terminator sequences are downstream of coding sequences, i.e. on the 3' position of the coding sequence. The terminator can e.g. be at least 1, at least 10, at least 30, at least 50, at least 100, at least 150, at least 200, at least 250, at least 300, at least 400, at least 500 nucleotides downstream of the coding sequence or directly adjacent. In combination thereto or independently therefrom the terminator sequence can be less than 10000, less than 8000, less than 6000, less than 5000, less than 4500, less than 4000, less than 3500, less than 3000, less than 2500, less than 2000, less than 1500, less than 1000, less than 750, less than 500, less than 250, less than 100 nucleotides downstream of the coding sequence.

In a preferred embodiment of the invention the polynucleotide may comprise a third transcription termination signal, optionally comprising or encoding a RNA hairpin structure (such as defined above, however being independently selected from any other hairpin terminator, or other), said third transcription termination signal being at most 1000 nucleotides apart from the first or second transcription termination signal. The first, second and optionally third terminator may be placed at the end of a (the same) gene or coding sequence to stop transcription of said gene or coding sequence. The polynucleotide may comprise further terminators.

The nucleotide distance between the first and second terminator, between the first and third and/or between the second and the third may each be individually be selected from any of the following ranges of at most 1000 nucleotides, at most 900 nucleotides, at most 800 nucleotides, at most 700 nucleotides, at most 600 nucleotides, at most 500 nucleotides, at most 400 nucleotides, at most 300 nucleotides, at most 250 nucleotides, at most 200 nucleotides, at most 180 nucleotides, at most 160 nucleotides, at most 150 nucleotides, at most 140 nucleotides, at most 130 nucleotides, at most 120 nucleotides, at most 110 nucleotides, at most 100 nucleotides, at most 90 nucleotides, at most 80 nucleotides, at most 70 nucleotides, at most 60 nucleotides, at most 50 nucleotides. Furthermore, The nucleotide distance between the first and second terminator, between the first and third and/or between the second and the third may each be individually be selected from any of the following ranges of at least 10 nucleotides, at least 15 nucleotides, at least 20 nucleotides, at least 30 nucleotides, at least 40 nucleotides, at least 50 nucleotides, at least 60 nucleotides, at least 70 nucleotides, at least 80 nucleotides. The placement of the terminators on the polynucleotide may allow an operable positioning that influences termination of the other terminators.

A hairpin is a stem-loop sequence comprising intramolecular base pairing and is a pattern that can occur in single-stranded DNA or, more commonly, in RNA. The structure is also known as a hairpin loop. It occurs when two regions of the same strand, mostly complementary in nucleotide sequence when read in opposite directions, base-pair to form a double helix that ends in an unpaired loop. The formation of a stem-loop structure is dependent on the stability of the resulting helix and loop regions. Obviously, the first prerequisite is the presence of a sequence that can fold back on itself to form a paired double helix. The stability of this helix is determined by its length, the number of mismatches or bulges it contains (a small number are tolerable, especially in a long helix) and the base composition of the paired region. Pairings between guanine and cytosine have three hydrogen bonds and are more stable compared to adenine-uracil pairings, which have only two. In RNA, guanineuracil pairings featuring two hydrogen bonds are as well common and favourable. Base stacking interactions, which align the pi orbitals of the bases' aromatic rings in a favourable orientation, also promote helix formation.

In especially preferred embodiments the hairpin structure is defined by a sequence Y-X-Z, wherein Y is a nucleotide sequence of at least 8 nucleotides in length and with a G/C content of at least 40%, preferably at least 50%, especially preferred at least 60%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z (and also not internally within X). Preferably X has 3, 4, 5, 6, 7 or 8 nucleotides in length. This general structure can be further TE improved by increasing the G/C content of the stem, optimizing the loop and increasing complementarity between Y and Z. Tetraloop (length of 4) structures for X are especially preferred. X may comprise or consists of the sequence U/T-NNG or vice-versa, with N being any nucleotide selected from U(T), A, C, G; preferably the sequence U/T-NNG is U/T-NCG, especially U/T-U/T-CG. A tetraloop with an adjacent G/C on Y and Z forms very stable loop structures that showed a very high termination efficiency and are among the most preferred embodiments of the invention.

Such a hairpin structure of formula X-Y-Z may be in the first, second and/or third transcription termination signal. Further termination signals may comprise other hairpin terminators or alternative non-hairpin (e.g. class II) terminators, or of course also a terminator of hairpin formula X-Y-Z, with Y, X and Z being selected independently. In preferred embodiments the polynucleotide of the invention comprises two hairpin terminators, especially preferably one or two being of the inventive X-Y-Z structure.

The invention also provides a polynucleotide comprising at least one transcription termination signal comprising a hairpin structure having said sequence Y-U/T-NNG-Z, wherein Y is a nucleotide sequence of at least 10 nucleotides in length and with a G/C content of at least 60%, Z is a nucleotide sequence with at least 70% complementarity to Y, the complementary nucleotides of Z being base paired with the nucleotides of Y, and sequence U/T-NNG being a loop with no base pairing to Y or Z, with N being any nucleotide selected from T(U), A, C, G; preferably the sequence U/T-NNG is U/T-U/T-CG. Such a polynucleotide, having the above described Y-X-Z structure with X being U/T-NNG (of course optionally also being included vice-versa), may comprise only one terminator, in particular placed independently from other terminators, e.g. operatively linked to an ORF or a cloning site where an ORF may be inserted. The above and the following where referring to a X-Y-Z hairpin applies to all aspects of the invention.

A high G/C content in the stem of the hairpin (Y or Z or in both together) is energetically favourable and leads to a highly stable hairpin, in turn increasing termination efficiency. In preferred embodiments the G/C content is at least 50%, at least 52%, at least 54%, at least 56%, at least 58%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75% of the nucleotides of either Y or Z or both.

In preferred embodiments at least one transcription termination signal (the first, second and/or third) comprises a A/T(U)-rich region of at least 4, preferably at least 5, at least 6, at least 7, at least 8, at least 9, or at least 10, nucleotides in length comprising at least 75%, A or T(U), wherein preferably said A/T(U)-rich region is downstream of a hairpin, in particular preferred not more than 20 nucleotides apart from said hairpin. The A/T(U)-rich region may comprise at least 3, at least 5, at least 6, at least 7, at least 8, at least 9, or at least 10, nucleotides selected from A/T(U) with preferably at most 1, at most 2, at most 3 G/C nucleotides. Especially preferred the A/T(U)-rich region is at most 20 nucleotides, preferably at most 15 nucleotides, at most 12 nucleotides, at most 10 nucleotides, at most 8 nucleotides, at most 7 nucleotides, at most 6 nucleotides, at most 5 nucleotides, at most 4 nucleotides, at most 3 nucleotides, at most 2 nucleotides, at most 1 nucleotide apart (usually downstream) from the hairpin or directly adjacent. The A/T(U)-rich region may be T(U)-rich and preferably comprises at least 3 T(U), at least 4 T(U), at least 5 T(U), at least 6 T(U), at least 7 T(U) or at least 8 T(U). The A/T(U)-rich region can be up to 20, up to, 15, up to 12, up to 10, up to 8 nucleotides in length. An A/T(U)-rich region downstream of the hairpin usually increases termination efficiency. It may be overlapping with the stem (Z). In this case preferably the last 1, 2, 3, 4 or 5 nucleotides of Z may be A or T(U), preferably T(U).

In the inventive hairpin of formula Y-X-Z, preferably Y is of 9, 10, 11, 12, 13, 14, 15, 16, 17, 18, 19, 20, 21, 22, 23, 24, 25, 26, 27, 28, 29, or 30 nucleotides in length. The length of Y determines the length of Z (by complementarity, which can be selected from the same nucleotide lengths. The length of substantially complementary Y and Z, the stem of the hairpin, determines the stem length in basepairs. The stem is not necessarily 100% complementary as described below, but has limited non-complementary opposing bases for Y and Z.

In particular, Y and Z can be of m nucleotides in length, where Y consist of the nucleotides $y_1$ to $y_m$ and Z consists of the nucleotides $z_1$ to $z_m$, the hairpin consists of the sequence $y_m y_{m-1} y_{m-2} \ldots y_8 y_7 y_6 y_5 y_4 y_3 y_2 y_1$-X-$z_1 z_2 z_3 z_4 z_5 z_6 z_7 z_8 \ldots z_{m-1} z_m$. Preferably $z_1$ is complementary to $y_1$ and $z_m$ is complementary to $y_m$ meaning that the end points of the stem of the hairpin are complementary. Furthermore any one of $y_a$ can be complementary to $z_a$, with a being an integer from 1 to m, especially complementarity between $y_a$ and $z_a$ can be for a being 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 and any combination thereof. Especially preferred the first and/or last 1, 2, 3, 4 or 5 nucleotides of the stem are complementary.

Y and Z should have a high complementarity for efficient and stable hairpin formation, e.g. Y and Z are at least 80% complementary, preferably at least 82%, at least 84%, at least 85%, at least 86%, at least 88%, at least 90%, at least 92%, at least 94%, at least 95%, at least 96%, at least 97%, at least 98%, at least 99%, or even 100%, complementary. The complementarity is most preferably with at least 70%, preferably at least 75%, at least 80%, at least 85%, at least 90%, at least 95% or at least 100%, G-C or A-T(U) complementarity.

In the stem structure formed by X and Z non-complementarites should be limited. Some limited non-complementarites are possible but should not be placed adjacent to each other in order to prevent formation of a "bubble" or additional loop. In preferred embodiments, in the hairpin, between nucleotides of Y and Z, at most 3, 2 or 1 G-U complementarities are adjacent to another G-U complementarity, preferably the hairpin being without adjacent G-U complementaries.

An especially preferred terminator of the invention is encoded by SEQ ID NO: 4. The present invention extends to further homologous terminators with at least 50%, at least 60%, at least 70%, at least 80%, at least 85%, at least 90%, at least 92%, at least 94%, at least 95%, at least 96%, at least 97%, at least 98% or at least 99% sequence identity to the terminator encoded by SEQ ID NO: 4. Preferably the non-identities remain as defined above and e.g. form no or limited non-complementary stem structures or A/T rich regions as described. SEQ ID NO: 4 describes an artificial optimized terminator with a stem (nts 1 to 16, 21 to 36) a loop (nts 17 to 20) and a A/U rich region following the stem (nts 37 to 40). It has a G/C content of 78% in the stem structure (25/32 nts).

In preferred embodiments at least on of the terminators of the inventive polynucleotide is a class II terminator.

In contrast to usual hairpin like terminators the termination event, action of class II terminators requires the presence of the non-coding strand, thus is a double strand driven process (He et al., J Biol Chem 267, 1998: 19306-19312). Further evidence, that transcriptional termination at these novel sequences, so called class II termination signals, is mediated through a mechanism independent from class I termination pathway, stems from in vitro transcription analyses with a mutated T7 RNA polymerase. Mutations between the 20 kDa N-terminal portion and the 80 kDa C-terminal fragment lead to a 'nicked' form of the polymerase, which is not able to terminate at class II termination signals, but is still able to stop elongation when transcribing hairpin containing class I termination signals (Lyakhov et al., J Mol Biol 269, 1997: 28-40). Thus, there are two different mechanism which can accomplish transcriptional termination in E. coli, and both pathways operate independently from each other.

Sequence analyses of putative organisms revealed the presence of further class II termination signals. These unusual sequences are present within the E. coli rrnB T1 termination site, in a cDNA copy of vesicular stomatitis virus (VSV), in adenovirus DNA, and within bacteriophage lambda DNA (Zhang and Studier, 1995) (Sousa et al., 1992). All these newly found sequences share a 7 bp long consensus sequence (ATCTGTT according to the non-template strand) and an unequally long run of uridines at the 3' end, comparable to the U-run at intrinsic termination signals Example class II terminators are:

```
                                          (SEQ ID NO: 9)
T7              tgtgtcccTATCTGTTacagtctcct (SEQ ID NO: 10)
PTH             atgcttgccATCGTTtcttgcaag (SEQ ID NO: 11)
VSV             atccatgaTATCTGTTagttttttc (SEQ ID NO: 12)
VSV-XhoI        atccatgaTATCTGTTctcgagttttttt (SEQ ID NO: 13)
rrnB T1         tttcgtttTATCTGTTgtttgtcgtg (SEQ ID NO: 14)
Adeno5          tagttttgTATCTGTTttgcagcagc (SEQ ID NO: 15)
lambda P1       ttcgaaccTcTCTGTTtactgataag
(from Lyakhov et al., J Mol Biol 280 (1998):
201-213)
```

The consensus sequence lacking the adjacent run of uridines (T in the non-template strand) is present at the right end of the concatemer junction (CJ) of replicating T7 DNA (Lyakhov et al., 1997). Because of the absence of an uridine tract, the importance of this 7 bp long sequence was previously analysed by mutating the intrinsic T7 polymerase into the "nicked" form. Phages expressing the nicked T7 polymerase aren't able to recognize potential class II termination sites.

According to the present invention the inventive class II terminator comprises the consensus sequence TCTGTT common to all 7 examples, in particular preferred, a T is within 2 nucleotides 3' of said TCTGTT sequence. Preferably the class II terminator comprises a sequence of at least 20 nucleotides, preferably at least 22, at least 24 or at least 26 nucleotides, in length with a T content of at least 40% (including the consensus sequence). A T-rich region of at least 40% T within 8 nucleotides in length is 3' or 5' adjacent to the consensus sequence.

The class II termination signal can be adjacent to a hairpin termination signal. Such class II terminators can be directly in front or after a hairpin with few or no intermediate nucleotides, preferably with at most 10, 9, 8, 7, 6, 5, 4, 3, 2, 1 or no intermediate nucleotides. An A/T(U)-rich, especially T(U) rich region following the hairpin may be between the hairpin and the adjacent class II terminator.

In vitro transcription assays using a template containing the class II termination site present in PTH gene, revealed a termination efficiency of about 55%, thus that terminator is less efficient than the hairpin forming T7 terminator (native T7 terminator sequences shows a TE of about 80%). However, according to the present invention it was found that in combination class I and class II terminators have a surprisingly increased overall efficiency.

Possibilities of the inventive polynucleotide comprising at least two terminator signals, being operatively linked, are:

1) A first terminator signal comprising a hairpin structure defined by a sequence Y-X-Z, wherein Y is a nucleotide sequence of at least 14 nucleotides in length and with a G/C content of at least 60%, preferably at least 65%,
X is a nucleotide sequence of 3 to 9 nucleotides in length, and
Z is a nucleotide sequence with at least 90% complementarity to Y,
the complementary nucleotides of Z being base paired with the nucleotides of Y, and X being a loop with no base pairing to Y or Z (and also not internally within X);
a second terminator signal comprising a hairpin structure defined by a sequence Y-X-Z, wherein Y is a nucleotide sequence of at least 8 nucleotides in length and with a G/C content of at least 40%, preferably at least 50%, especially at least 60%,
X is a nucleotide sequence of 3 to 9 nucleotides in length, and
Z is a nucleotide sequence with at least 70% complementarity to Y,
the complementary nucleotides of Z being base paired with the nucleotides of Y, and X being a loop with no base pairing to Y or Z (and also not internally within X); with the first and second terminator being at most 1000 nucleotides apart to provide a concerted termination by the first an second termination signal. Y, X, and Z of the first and second terminator can be selected independently as described above. The terminator signals can be in any order or in order as listed above.

2) A first terminator signal comprising a hairpin structure defined by a sequence Y-X-Z, wherein Y is a nucleotide sequence of at least 12 nucleotides in length and with a G/C content of at least 60%, preferably at least 65%,
X is a nucleotide sequence of 3 to 9 nucleotides in length, and
Z is a nucleotide sequence with at least 80% complementarity to Y,
the complementary nucleotides of Z being base paired with the nucleotides of Y, and X being a loop with no base pairing to Y or Z (and also not internally within X);
a second terminator signal comprising a class II termination signal, preferably comprising the consensus sequence TCTGTT, especially preferred comprising a sequence of at least 20 nucleotides in length with a T content of at least 40%; Y, X, and Z of the first and optional further terminators and the parameters of the class II termination signal can be selected independently as described above. The terminator signals can be in any order or in order as listed above. The class II termination signal can be adjacent to one of the above or a further hairpin termination signal.

3) A first terminator signal comprising a hairpin structure defined by a sequence Y-X-Z, wherein Y is a nucleotide sequence of at least 12 nucleotides in length and with a G/C content of at least 60%, preferably at least 65%,
X is a nucleotide sequence of 3 to 9 nucleotides in length, and
Z is a nucleotide sequence with at least 80% complementarity to Y,
the complementary nucleotides of Z being base paired with the nucleotides of Y, and X being a loop with no base pairing to Y or Z (and also not internally within X);
a second terminator signal comprising a hairpin structure defined by a sequence Y-X-Z, wherein Y is a nucleotide sequence of at least 8 nucleotides in length and with a G/C content of at least 40%, preferably at least 50%, especially at least 60%,
X is a nucleotide sequence of 3 to 9 nucleotides in length, and
Z is a nucleotide sequence with at least 70% complementarity to Y,
the complementary nucleotides of Z being base paired with the nucleotides of Y, and X being a loop with no base pairing to Y or Z (and also not internally within X);
a third terminator signal comprising a hairpin structure defined by a sequence Y-X-Z, wherein Y is a nucleotide sequence of at least 8 nucleotides in length and with a G/C content of at least 40%, preferably at least 50%, especially at least 60%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z (and also not internally within X); with the first, second and third terminator being at most 1000 nucleotides apart to provide a concerted termination by the first, second and third termination signal. Y, X, and Z of the first, second or third terminator can be selected independently as described above. The terminator signals can be in any order or in order as listed above.

4) A first terminator signal comprising a hairpin structure defined by a sequence Y-X-Z, wherein Y is a nucleotide sequence of at least 12 nucleotides in length and with a G/C content of at least 60%, preferably at least 65%, X is a nucleotide sequence of 3 to 9 nucleotides in length, and Z is a nucleotide sequence with at least 80% complementarity to Y, the complementary nucleotides of Z being base paired with the nucleotides of Y, and X being a loop with no base pairing to Y or Z (and also not internally within X);

a second terminator signal comprising a class II termination signal, preferably comprising the consensus sequence TCTGTT, especially preferred comprising a sequence of at least 20 nucleotides in length with a T content of at least 40%;

a third terminator signal comprising a hairpin structure defined by a sequence Y-X-Z, wherein Y is a nucleotide sequence of at least 8 nucleotides in length and with a G/C content of at least 40%, preferably at least 50%, especially at least 60%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z (and also not internally within X); with the first, second and third terminator being at most 1000 nucleotides apart to provide a concerted termination by the first, second and third termination signal. Y, X, and Z of the first or third terminator and the consensus and T-rich sequence of the class II termination signal can be selected independently as described above. The terminator signals can be in any order or in order as listed above. The class II termination signal can be adjacent to one of the above or a further hairpin termination signal.

5) A first terminator signal comprising a hairpin structure defined by a sequence Y-X-Z, wherein Y is a nucleotide sequence of at least 12 nucleotides in length and with a G/C content of at least 60%, preferably at least 65%, X is a nucleotide sequence of 3 to 9 nucleotides in length, and Z is a nucleotide sequence with at least 80% complementarity to Y, the complementary nucleotides of Z being base paired with the nucleotides of Y, and X being a loop with no base pairing to Y or Z (and also not internally within X);

a second terminator signal comprising a hairpin structure defined by a sequence Y-X-Z, wherein Y is a nucleotide sequence of at least 8 nucleotides in length and with a G/C content of at least 40%, preferably at least 50%, especially at least 60%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z (and also not internally within X) and a class II termination signal adjacent to the hairpin structure, preferably comprising the consensus sequence TCTGTT, especially preferred comprising a sequence of at least 20 nucleotides in length with a T content of at least 40%;

a third terminator signal comprising a hairpin structure defined by a sequence Y-X-Z, wherein Y is a nucleotide sequence of at least 8 nucleotides in length and with a G/C content of at least 40%, preferably at least 50%, especially at least 60%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z (and also not internally within X); with the first, second and third terminator being at most 1000 nucleotides apart to provide a concerted termination by the first, second and third termination signal. Y, X, and Z of the first, second or third terminator and the consensus and T-rich sequence of the class II termination signal can be selected independently as described above. The terminator signals can be in any order or in order as listed above. The class II termination signal can be adjacent to one of the above or a further hairpin termination signal.

Preferably the inventive polynucleotide is provided in a form suitable for easy handling, e.g. being of limited length. The polynucleotide may thus exclude genomic sequences or large genomic fragments. In preferred embodiments the polynucleotide comprises up to 30,000 nts (nucleotides), up to 25,000 nts, up to 20,000 nts, up to 15,000 nts, up to 12,500 nts, up to 10,000 nts, up to 9,000 nts, up to 8,000 nts, up to 7,000 nts, up to 6,000 nts.

The inventive polynucleotide preferably comprises one or more restriction sites flanking said transcription termination signals and/or a cloning site upstream of the transcription termination signals, or a coding sequence (CDS) upstream of the transcription termination signals, preferably further operatively linked to a promoter. Such polynucleotides allow functionally high rates of termination during transcription of the operatively linked CDS. A CDS of choice can be inserted by providing restriction sites on the polynucleotide molecule. The inventive terminators may be operatively positioned for termination of a transcript of a multiple cloning site (into which a coding sequence might be inserted). The term "multiple cloning site" refers to a site comprising at least 2 sites for restriction enzymes, however, preferably it comprises a number of sites for various restriction enzymes.

A promoter can be used to initiate transcription. Preferably a T7 RNA polymerase promoter is used. In preferred embodiments the polynucleotide is flanked by endonuclease restriction sites at its 5' and/or 3' terminus. Terminal restriction sites allow easy handling of the inventive polynucleotide for incorporation into other nucleic acid molecules, such as vectors or expression cassettes.

The inventive terminator sequences work in particular well with the use of the T7 RNA polymerase. In preferred embodiments the inventive polynucleotides with the new terminator sequences can be obtained from any polynucleotide or vector which comprises a T7 terminator and replacing the T7 terminator by the inventive terminator sequences.

The T7 terminator has its origins in the genome of bacteriophage T7 and has since been widely used in synthetic vectors, such as plasmid vector pET30. In the commercially available pET30a vector (Novagen, Merck kgaA, HE, Germany; FIG. 1; SEQ ID NO:1, reverse complementary sequence: SEQ ID NO:2) the T7 terminator DNA sequence (SEQ ID NO: 3) is found on the reverse complementary sequence (SEQ ID NO: 2) at position 5345 to 5417. The T7 terminator is further used in vectors pIGDMCT7RS (NCBI database DQ485721.1), pLM99 (NCBI database AF308739.1), pLM100 (NCBI database AF308740.1), pLM101 (NCBI database AF308741.1), pXZ240 (NCBI database AF316555.1), pJH391 (NCBI database AF316554.1), pJH370 (NCBI database AF316553), pT7RS (NCBI database AY923866.1), pLM3 (NCBI database AF179892.1), pLS13 (NCBI database AF169190.1), pLS3 (NCBI database AF169189.1), pZH3 (NCBI database AF168612), pBIT (NCBI database JF275063.1), pNit::ET (NCBI database GU459073.1), pYUBDuet (NCBI database HQ247815.1), pYUB28b (NCBI database HQ247814.1), pSB4316 (NCBI database HQ343239.1), just to name a few. Further vectors with the T7 terminator can be easily determined by a BLAST search in available nucleotide sequence databases, such as NCBI database, EMBLEBI database, DDBJ databank. The BLAST program is publicly available from NCBI and other sources (BLAST Manual, Altschul, S., et al., NCBI NLM NIH Bethesda, Md. 20894; Altschul, S., et al., J. Mol. Biol. 215: 403-410 (1990). Functional equivalent terminators can be found in further sequences with at least 50%, at least 60%, at least 70%, at least 80%, at least 85%, at least 90%, at least 92%, at least 94%, at least 95%, at least 96%, at least 97%, at least 98% or at least 99% sequence identity to SEQ ID NO: 3. Any such sequences and vectors can be used for modifying the transcription termination according to the transcription termination signals according to the present invention.

In a further embodiment of the present invention an expression cassette is provided which comprises a sequence of a nucleic acid as defined above and a sequence of a gene product (i.e. a coding sequence, ORF) wherein the terminator sequence of the invention is operatively positioned for termination of transcriptional of the gene product. The expression cassette may also be isolated and/or purified. Such expression cassettes may e.g. be provided in a vector suitable for transfection of a host cell. Also, the expression cassette may be provided in a modified genome of a host cell. The genome can e.g. be modified by recombinant techniques, in particular knock-in procedures or providing an artificial chromosome.

Preferably the inventive expression cassette is provided in a form suitable for easy handling, e.g. being of limited length. The expression cassette may thus exclude genomic sequences or large genomic fragments. In preferred embodiments the expression cassette comprises up to 30,000 nts, up to 25,000 nts, up to 20,000 nts, up to 15,000 nts, up to 12,500 nts, up to 10,000 nts, up to 9,000 nts, up to 8,000 nts, up to 7,000 nts, up to 6,000 nts. In preferred embodiments the expression cassette is flanked by endonuclease restriction sites at its 5' and/or 3' terminus.

In further preferred embodiments the expression cassette comprises intron sequences which are not translated and excised between transcription and translation. Such intron sequences may e.g. be located between a promoter sequence and a start codon of a coding sequence or within the coding sequence. It has been found that such intron sequences can increase gene expression due to a mechanistical relationship with transcript processing.

In a further aspect of the invention a vector is provided comprising a sequence of a nucleic acid molecule as defined above. The vector may also comprise the expression cassette as mentioned above. It can be isolated and/or purified. Preferably the vector is a biological functional vector such as an expression vector or a phage.

The inventive sequence having gene transcription termination activity is preferably positioned flanking an endonuclease site. This allows easy cloning of coding sequences into this vector operatively linked to the inventive sequences with terminator activity. A plasmid might comprise one or more of the following: A prokaryotic origin of replication, a marker or antibiotic resistance gene sequence, in addition to a multiple cloning site or a coding sequence operably positioned with the inventive terminators.

In a further embodiment the invention relates to a cell comprising a polynucleotide or an expression cassette or a vector as defined above. In preferred embodiments the polynucleotide, expression cassette or vector is stably integrated into the genome of said cell. Alternatively, it is also possible to incorporate these polynucleotides, expression cassettes or vectors transiently.

The cell should be suitable to express a gene product from the inventive polynucleotide. A suitable host cell for expressing a gene product are e.g. prokaryotic, eukaryotic, yeast, especially bacterial, mammal, avian, plant or insect cells. In preferred embodiments the cells express the T7 RNA polymerase, which is extremely accurate and just transcribes DNA sequences provided with a T7 promoter sequence capable of recognizing hairpin terminators (class I terminators)—wild type and nicked form T7 polymerase—and optionally also class II terminators—wild type but not nicked form T7 polymerase. Compared to E. coli RNA polymerase, T7 polymerase transcribes up to five. Expression of T7 RNA polymerase can be either endogenously (e.g. by the host cell, in particular T7 polymerase being encoded by the genome of the host cell) or by artificial transfection (e.g. T7 polymerase being in a vector but may also be integrated into the genome). Preferably the cells are prokariotic, especially E. coli. Preferably the cells are of a bacterial cell culture, preferably of a non-pathogenic culture like non-pathogenic strains of E. coli, e.g. strain MG1655, BL21, HMS174 or DE3 lysogens of the said strains.

In a further aspect the inventive polynucleotides, the expression cassettes or the vectors can be used for the expression (or production) of a gene product. One example is a method of expressing a gene product, preferably a protein, comprises transfecting an isolated cell or cell line in an expression cassette according to the invention and expressing the gene product, optionally further comprising isolating the expressed gene product. The inventive method of producing a gene product may comprise providing a cell as described above and cultivating said cell under conditions allowing expression of said gene.

Alternatively, a gene product can be expressed ex vivo in a synthetic/extracellular translation system.

The invention provides an in vitro method of producing a mRNA, comprising providing a polynucleotide with the inventive terminator signal and a coding sequence upstream of said transcription termination signal and contacting said polynucleotide with the T7 RNA polymerase. In vitro transcription requires a polynucleotide template, usually DNA, containing a promoter, ribonucleotide triphosphates, a buffer system that includes magnesium ions, and an appropriate phage RNA polymerase, preferably the T7 RNA polymerase. The produced mRNA can then be used for analytical uses and/or to express a gene product. The most frequently used cell-free translation systems consist of extracts from rabbit reticulocytes, wheat germ and *Escherichia coli*. All are prepared as crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract should be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors known in the art.

A further aspect of the invention relates to a polynucleotide molecule comprising a sequence complementary to one of the inventive sequences having terminator activity. Such a complementary molecule usually binds to the inventive sequence as so called "anti-terminator". Anti-terminators are e.g. described in Sooncheol et al. (Nucleic Acids Research 38(18), 2010:6045-6053). The complementary molecules preferably bind to the stem-loop sequence of the inventive terminator and prevent or hinder proper stem formation by competitively binding to at least one part of the stem sequence. Preferably the anti-terminator is complementary to 3, 4, 5, 6, 7 or more nucleic acids of the stem sequence. Such complementary sequences can be e.g. used to stably bind the inventive sequence having terminator activity to e.g. control expression of a gene. Upon stable binding of such a complementary sequence, termination may be enhanced or suppressed, in particular suppressed. The nucleic acid molecule with the complementary sequence may be of any nucleotide type, preferably nucleotide types which strongly bind to a DNA molecule with the inventive sequence having terminator activity. Such nucleic acid types with high binding ability are e.g. RNA, LNA (locked nucleic acids), or PNA (peptide nucleic acids).

The present invention further relates to a method of controlling termination and/or expression of a gene product by an expression cassette as defined above, comprising administering to a cell with the expression cassette a nucleic acid molecule with a complementary sequence as mentioned above.

The present invention is further illustrated by the following figures and examples without being limited to these exemplary embodiments of the invention.

EXAMPLES

1. Materials and Methods 1.1: Bacterial Strains

For cloning procedures *E. coli* strain DH5α (F− endA1 glnV44 thi-1 recA1 relA1 gyrA96 deoR nupG Φ80dlacZΔM15 Δ(lacZYA-argF)U169, hsdR17(rK− mK+), λ−) was used as host and *E. coli* HMS174(DE3) (F− recA1 hsdR(rK12− mK12+) (DE3) (RIf R)) (Novagen, Merck KgaA, HE, Germany) was used as production strain. Thus expression of T7 polymerase is inducible by addition of IPTG.

1.2: Plasmids

Figure 1:
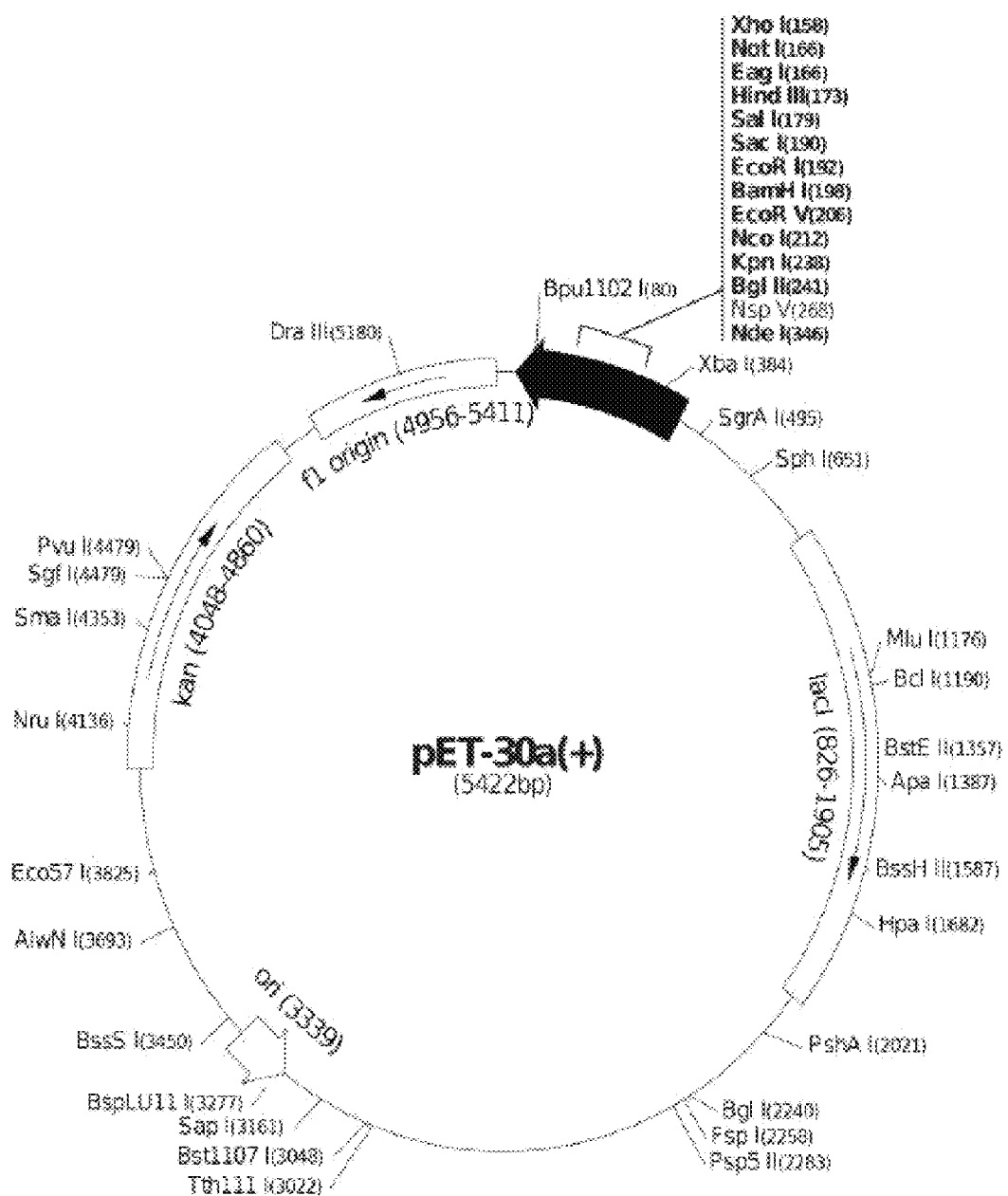
FIG. 1: (SEQ ID NOS: 24-33) Plasmid map of expression plasmid pET30a (Novagen, Merck KgaA, HE, Germany).

As standard expression vector pET30a (Novagen, Merck KgaA, HE, Germany; see FIG. 1; SEQ ID NOs: 1 and 2) was utilized. The plasmid carries a kanamycin resistance gen and a putative gen coding for repressor molecule LacI. For cloning of foreign DNA numerous restriction sites within the multiple cloning site (MCS) are available. Inserted gen is under the control of the inducable T7/lac hybrid promoter and transcription, mediated by T7 polymerase, gets stopped by a single T7 termination signal at the 3' end. Replication is mediated through a ColE1 like origin of replication.

1.3: Expression Genes

Recombinant human superoxiddismutase (rhSOD) was chosen as model protein. Up to now no toxic effect of hSOD when expressed in *E. coli* could be observed, thus the cellular burden on the host, triggered by expression of the foreign gen, is solely caused by the level of production rate (qP).

hSOD complexed with Cu/Zn in its active centre participates in antioxidant defence in the cytoplasm of nearly all cells exposed to oxygen. Especially erythrocytes and liver cells possess a high level of active hSOD enzymes, catalysing the reduction of two oxygen radicals, resulting in the formation of hydrogen peroxide. The protein has a molecular weight of 32 kDa and in its active form the enzyme consists of two not covalently bound identical subunits (153 AA each), complexed with one Zn and one Cu atom in its active centre.

The gene coding for hSOD was amplified with primers containing recognition sequences of restriction enzymes XbaI and BamHI at their 5' ends (primers GTCGTCGGATCCTTACTATTGGGCGATCCC (SEQ ID NO: 5) and GTCGTCTCTAGAAATAATTTTGTTTAAC (SEQ ID NO:6)). The resulting fragment was used for cloning the hSOD gene into a original pET30a vector.

1.4: Cloning methods

Cloning procedures were done according to (Sambrook and Russel, 2001). Restriction enzymes and other modifying enzymes were purchased from New England Biolabs (Ipswich, Mass., USA) and applied according to the manufacturer's recommendations. All primers and synthetic oligonucleotides were acquired from Sigma Aldrich (St. Louis, Mo., USA).

Primer design, in silico cloning, sequence analysis and secondary structure prediction was done with CLC main workbench. Correct insertion of fragments was confirmed using PCR over the adequate sequence region and amplification products were verified with regard to length through agarose gel electrophoresis. Clones possessing a correct cloning product were amplified in liquid medium and the respective plasmid was isolated using a standard plasmid preparation kit (Wizard Plus SV Minipreps DNA purification System from Promega, Cat. No: A1330). Purified plasmids were sent to AGOWA (AGOWA genomics GmbH, B, Germany) for sequencing. Due to the fact that most of the samples contain sequence regions showing pronounced secondary structures, sequencing was done in the presence of denaturing reagents in single economy read mode.

1.5: Intrinsic Terminator Deletion

In order to investigate the role of an insufficient transcriptional termination on deregulation of plasmid copy number control, a pET30a derivative lacking the intrinsic T7 terminator was produced. As starting material the original pET30 plasmid with the cloned (XbaI/BamHI) hSOD as model protein was used. That plasmid was named Plasmid_I and functions as reference plasmid for all subsequent analyses.

To delete the intrinsic T7 termination signal on the original pET30a plasmid an inverse PCR was designed. Primers are constructed to bind to DNA templates in opposite direction according to their 3' end (primers TTAGCAGCCGGATCTCAGTGGTGG (SEQ ID NO: 7) and GGAGGAACTATATCCGGATTGGCG (SEQ ID NO: 8). Thus the DNA sequence present between the two primers binding sites gets deleted. Again KOD Hifi Polymerase (Merck KgaA, HE, Germany) was chosen for PCR reaction. The resulting plasmid was named Plasmid_J and is 104 bp shorter than Plasmid_I, which was used as template. The correct deletion of the termination signal was confirmed by sequencing the appropriate region.

1.6: In Vitro Transcription

After construction of several pET30a derivatives possessing altered termination signals, their individual capability to terminate T7 polymerase mediated transcription was verified by using AmpliScribe™ T7 High Yield Transcription Kit from Epicentre Biotechnologies (Biozym Scientific GmbH, NI, Germany).

As template pure plasmid solutions purified with QIAfilter Plasmid Midi kit were employed. Prior to use templates were linearised by restriction with SmaI. That restriction site is present in all templates and after digest a double stranded DNA with blunt ends is produced. The SmaI site is located about 1000 bp downstream of the MCS of pET30a, representing the longest possible transcription product. Termination products and readthrough products differ in size of about 1000 bp and were distinguishable after separation by electrophoresis. About 2 μg of distinct templates DNA was digested with SmaI for 3 h at 25° C. Subsequently the restriction enzyme was inactivated by incubation at 65° C. for 20 min and the reaction mixture was purified with Wizard SV Gel and PCR Clean-Up System. A volume containing about 200 ng of linearised and purified plasmid DNA was used for subsequent in vitro transcription.

The whole transcription approach was incubated at 37° C. for 2 h-3 h. Subsequently the optional Dnase I digest was carried out in order to get rid of template DNA. For that purpose 1 μL of Rnas-Free Dnase I solution (1 MBU/μl) was added to the in vitro transcription reaction mixture and digest was done for additional 15 min at 37° C. One Molecular Biology Unit (MBU) of Dnase I is defined as amount of enzyme sufficient to digest 1 μg of pUC19 DNA to oligodeoxynucleotides in 10 minutes at 37° C.

1.7: Transcript Analysis and Calculation of Termination Efficiency (TE)

Purified RNA samples were analysed according to their size and quantity using the Bioanalyzer 2100 system provided from Agilent Technologies (Santa Clara, Calif., USA). In principle the system relies on traditional electrophoresis but has been transferred to chip format, by etching micro channels into glass serving as supporting material. The chip format dramatically reduces separation time as well as sample and reagent consumption. In detail just 1 μl comprising RNA of 25 ng-250 ng are sufficient for a single run. The system provides automated sizing and quantification information in a digital format.

For separation the micro channels get filled with a sieving polymer and fluorescence dye. After loading the samples a voltage is applied, thus charged biomolecules like nucleic acids migrate to positively charged pole. Because of a constant mass-tocharge ratio and the presence of a sieving polymer matrix, the molecules are separated by size. Smaller fragments are migrating faster than larger ones. Dye molecules intercalate into DNA or RNA strands and those complexes are detected by laser-induced fluorescence measurement. Data are translated into gel-like images (bands) or electropherograms (peaks). With the help of a ladder that contains components of known sizes, a standard curve of migration time versus fragments size is plotted. From the migration times measured for each fragment in the sample, the size is calculated. The ladder also contains components of a distinct concentration, thus quantitation can be done by calculation of the ladder area and subsequent comparison with sample peak areas (http://www.chem.agilent.com).

For separation and quantification of in vitro transcribed RNA the Agilent RNA 6000 Nano LabChip® kit was used. Sample preparation and analysis was done according to the manufacturer's recommendations. For all runs approximately 1 µl containing 200 ng of RNA were loaded on the chip. Each in vitro transcription assay was verified by loading at least 3 samples on one chip. Most of the RNA samples stemming from one transcription assay were also verified by loading on two different chips. In both cases standard deviation of calculated termination efficiency (TE) varied in a very small range and never exceeded ±0.4. In rare cases TE was also calculated from different in vitro transcription assays, whereby calculated TE showed higher standard deviation values of about ±1%.

After separation of RNA transcripts according to their size, the amount of the respective RNA fraction was assessed by calculation of area peak and subsequent comparison to ladder area. Termination efficiencies were calculated as the molar ratio between terminated transcript and the sum of terminated and read-through transcripts, and an average of at least three measurements was taken.

1.8: Cell Cultivation Conditions

All fermentations were run in fed batch mode. Adjusted growth rate, amount of inducer and medium feed rate were subjected to induction strategies (see Process design and induction of recombinant protein). As inoculum 1 ml ($OD_{600}$) of a thawed master cell bank (MCB) vial was injected under aseptic conditions. Fermentation process was run under following process parameters and observed with indicated devices.

A 20 L bioreactor (14 L net volume, 4 L batch volume) from MBR Bioreactor AG (Wetzikon, Switzerland) was used, equipped with standard control units (Siemens PS7, Intellution iFIX). Temperature was maintained at 37° C.±0.5° C. and measured with a Pt100 temperature probe. pH was maintained at pH 7.0±0.05 by addition of 25% ammonia solution (ACROS Organics). For calibration commercially available buffer solutions were applied. Foaming was suppressed by addition of 0.5 ml antifoam (PPG 2000 Sigma Aldrich) per liter media.

$pO_2$ measurement was performed with a Clark probe. Calibration was done after sterilization of bioreactor at fermentation conditions (37° and 800 rpm). For setting point for 0% saturation $N_2$-gas or an $O_2$-simulator (Mettler Toledo) were used. For assigning 100% saturation compressed air was streamed in (12l/min). During fermentation $pO_2$ was constantly retained above 30% by regulating stirrer speed. When the maximum stirrer speed of 1200 rpm was reached, the inlet air flow was stepwise increased.

Substrate was added to the bioreactor following an exponential profile in order to keep the growth rate at the desired value. Feed control was achieved by increasing the pump speed according to the exponential growth algorithm, with superimposed feedback control of weight loss of the substrate tank. All chemicals were purchased from Merck unless otherwise noted. The minimal medium used for these cultivations contained 3 g $KH_2PO_4$ and 6 g $K_2HPO_4*3H_2O$ per liter. These concentrations provided the required buffer capacity and served as P- and K-source as well. The other components were added in relation to gram cell dry mass (CDM) to be produced: $Na_3$-citrate$*2H_2O$ (ACROS organics) 0.25 g, $MgSO_4*7H_2O$ 0.10 g, $CaCl_2*2H_2O$ 0.02 g, trace element solution 50 µl and glucose$*H_2O$ 3 g. Additional to the trace element solution for cultivations with recombinant hSOD 4 mg $CuCl_2*2H_2O$ and 3.2 mg $ZnSO_4*7H_2O$ per g CDM was added. Trace element solution: prepared in 5N HCl ($g*l^{-1}$): $FeSO_4*7H_2O$ 40.0, $MnSO_4*H_2O$ 10.0, $AlCl_3*6H_2O$ 10.0, $CoCl_2$ (Fluka) 4.0, $ZnSO_4*7H_2O$ 2.0, $Na_2MoO_2*2H_2O$ 2.0, $CuCl_2*2H_2O$ 1.0, $H_3BO_3$ 0.50.

The minimal medium for feeding phase was designed to achieve 386 g of CDM (30 g/L) in total. All components except glucose needed for the fed batch medium were mixed in a volume equivalent to about 5000 g. Glucose was separately dissolved in a volume equivalent to 3500 g. Both solutions were independently autoclaved and mixed together after cooling down. Nitrogen level was held by adding 25% ammonia solution for pH control. After mixing all together the net weight was determined and served as input for the automated feed control algorithm. To accelerate initial growth of the population, the complex component yeast extract (0.15 g/g CDM) was added to the minimal medium to the batch medium, moreover 2.5 g/L ammonium chloride ($NH_4Cl$) and 2.1 g/L ammonium sulphate (($NH_4)_2SO_4$) were added to avoid N-limitation in batch phase. The minimal batch medium was calculated to achieve 22.5 g CDM (5.62 g/L), and the components were dissolved in a volume equivalent to 3800 g. Glucose was again separately dissolved in a volume equivalent to 300 g. After autoclaving both solutions were aseptically combined.

Before induction of recombinant protein production cells were grown in not induced state in order to allow adaptation to fed batch conditions. After one doubling time (around 7 h) cells got induced with IPTG (isopropyl-β-D-thiogalactopyranoside). For induction two different strategies were implemented. In a first experimental design cells were fully induced by single addition of highly concentrated IPTG. The required amount of inducer was calculated to supply the expected CDM of 386 g at the end of the process with an IPTG concentration of 20 µmol/CDM (cell dry mass). That classical pulse induction is achieved by adding the IPTG solution aseptically with a syringe provided with a sterile filter directly into the bioreactor.

A second induction strategy was conducted according to Striedner et al. (Striedner et al., 2003, Biotechnol Prog 19: 1427-1432). Addition of limited amounts of inducer in a constant ratio to produced biomass allows a optimal exploitation of the cell's capacity to produce recombinant protein. IPTG concentration is maintained at a physiological tolerable level of 0.9 µmol/g CDM (limited induction conditions). As in classical approach cells also get induced after one generation by external addition of IPTG by using a syringe. Afterwards IPTG is fed according to the exponential regime. For that purpose an external inducer feed, similar to that arrangement conducted for the influx of feed medium, was implemented. A tank containing the inducer solution was put on a balance and IPTG was added according to the exponential growth of bacteria. Influx of inducer solution was controlled by adjusting pump speed and was controlled due to weight loss by an automated influx algorithm. An increase in biomass is encountered by an exponential feed of inducer, resulting in a constant ratio of inducer to biomass over the whole process. Reduction of the concentration of IPTG reduces the transcription rate, thus transcription of foreign genes is diminished to a more tolerable level, ending up in a higher product yield.

1.9: Process Monitoring

To determine the turbidity of the fermentation broth samples were measured with a spectrophotometer (Amersham Biosciences Ultrospec 500 pro, Pharmacia Biotech Ultrospec 1000E) at wavelength λ=600 nm. To ensure a measurement within linear range (OD$_{600}$=0.1-0.6), samples were diluted in RO—H2O and water was also used as reference.

To determine cell dry weight (CDW) 10 ml of cell material were aseptically taken out of the bioreactor and centrifuged for 10 min at 5000 rpm (Heraeus Laborfuge 200). Supernatant was discarded, cells were resuspended in 5 ml RO—H2O and centrifuged again. After removal of excess water, cells were suspended in RO—H2O again and immediately transferred to a pre-weighed beaker. All beakers were dried for 24 h at 105° C. and reweighed. For determination of total CDM in the bioreactor, the total broth volume at the time point at which samples were taken has to be calculated. The total volume in the bioreactor is given by summarizing the batch volume, the consumption of feed medium and the inflow of 25% ammonia solution. That value gets reduced by subtracting the volume of taken samples and is equal to the volume present in bioreactor at a distinct time point. Multiplying total volume with the determined CDM/ml displays the total CDM in the bioreactor at the moment of sample taking.

In order to determine plasmid stability, cells were plated on agar plates in the presence and the absence of kanamycin. Therefore 1 ml of an adequate cell dilution series was pipetted on a petri dish and mixed with 55° C. pre-warmed nutrient agar. In Accordance with its inventor that method is termed Koch plating.

In order to determine the number of plasmid molecules within a bacterial cell, the ratio of plasmid DNA (pDNA) to chromosomal DNA was calculated. pDNA was isolated by using a standard plasmid purification kit (Wizard Plus SV Minipreps DNA purification System from Promega, Cat. No: A1330). Measurement of total DNA was done fluorimetrically with Höchst dye H33258 after disruption of cells with lysozyme and SDS. To determine loss of pDNA during purification, samples were treated by addition of an internal standard (pUC19) before purification. After purification the amount of plasmid DNA and its integrity were analysed through capillary electrophoresis (Agilent 2100 Bioanalyzer).

Induced cells are highly stressed by producing recombinant protein, thus aren't able to proliferate in order to form colonies. To examine the number of antibiotic resistant, non producing cells, samples were also poured on agar plates containing kanamycin and IPTG. 1 ml of sample got diluted in physiologically active saline salt solution (0.9%) to a final dilution of 10-9. From each 10-7 to 10-9 dilution step 1 ml was plated three times together with pre-warmed nutrient broth agar without kanamycin and also in the presence of kanamycin (100 mg/l). From 10-3 to 10-5 dilutions 1 ml was poured on nutrient broth agar plates containing kanamycin (100 mg/l) and IPTG (200 mg/l). Plates were incubated for 24 h at 37° C. in order to counter colony forming units (CFU).

In order to quantify the amount of soluble hSOD in cytoplasm, an enzyme-linked immuno sorbent assay (ELISA) was performed. For that purpose hSOD gets immobilized by binding to primary SOD antibody, which in turn is fixed on the surface of an adequate micro-titer plate. After washing out excess reagents a second monoclonal mouse antibody is added. That secondary antibody recognizes the complex containing of primary antibody bound to hSOD and is linked to alkaline phosphatase, which is able to utilize the chromogenic substance p-Nitrophenylphosphat, resulting in formation of a yellowish product. The amount of coloured substance can be measured at 405 nm with a photometer, thus the intensity of emitted light correlates with the amount of bound hSOD and enables the quantification of produced recombinant protein.

Example 1: Terminator Design and In-Vitro Testing

Figure 3:
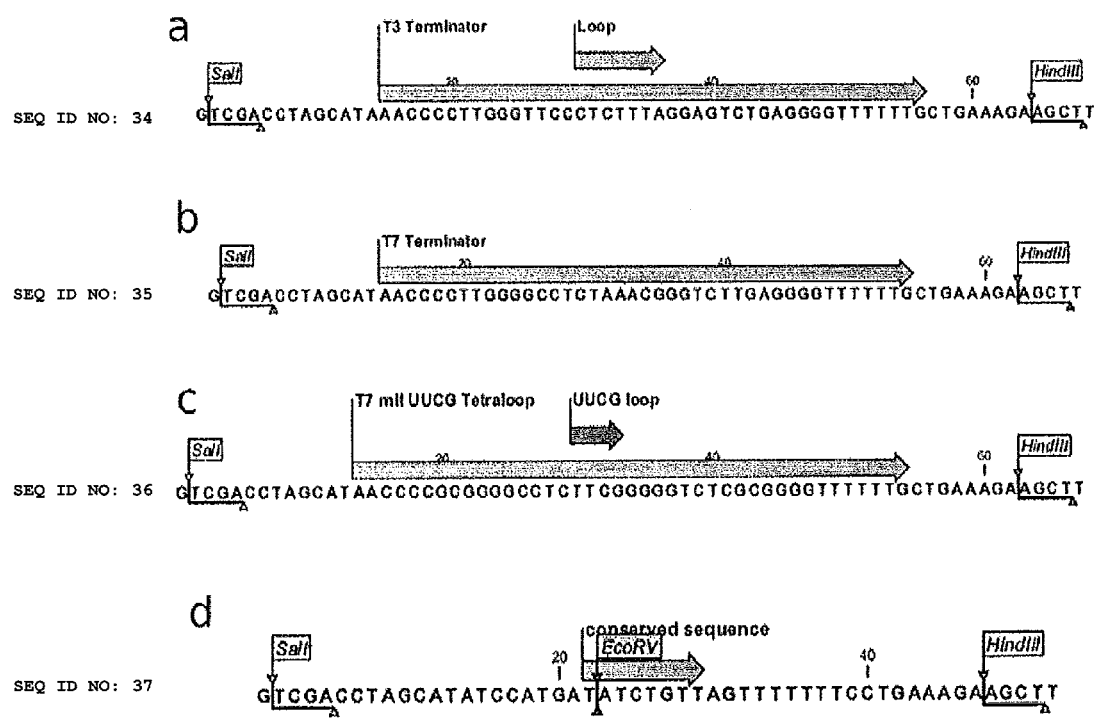
FIG. 3: Four termination signals (restriction sites are indicated). From top to bottom: the intrinsic terminator present in bacteriophage T3 (SEQ ID NO: 34), the original T7 terminator (SEQ ID NO: 35), the modified T7 terminator with the altered tetraloop (SEQ ID NO: 36), and the class II terminator stemming from VSV (SEQ ID NO: 37).

Four different terminators (see FIG. 3) were cloned (SalI/HindIII) upstream of the production plasmid pET30a (Plasmid_I) encoded T7 terminator. Inserted terminator sequences:

VSV:
(SEQ ID NO: 16)
TCGACCTAGCATATCCATGATATCTGTTAGTTTTTTCCTGAAAGA

T3:
(SEQ ID NO: 17)
TCGACCTAGCATAAACCCCTTGGGTTCCCTCTTTAGGAGTCTGAGGGGT-

TTTTTGCTGAAAGA

T7:
(SEQ ID NO: 18)
TCGACCTAGCATAACCCCTTGGGGCCTCTAAACGGGTCTTGAGGGGTTT-

TTTGCTGAAAGA

T7UUCG:
(SEQ ID NO: 19)
TCGACCTAGCATAACCCCGCGGGGCCTCTTCGGGGGTCTCGCGGGTTT-

TTTGCTGAAAGA

Figure 4:
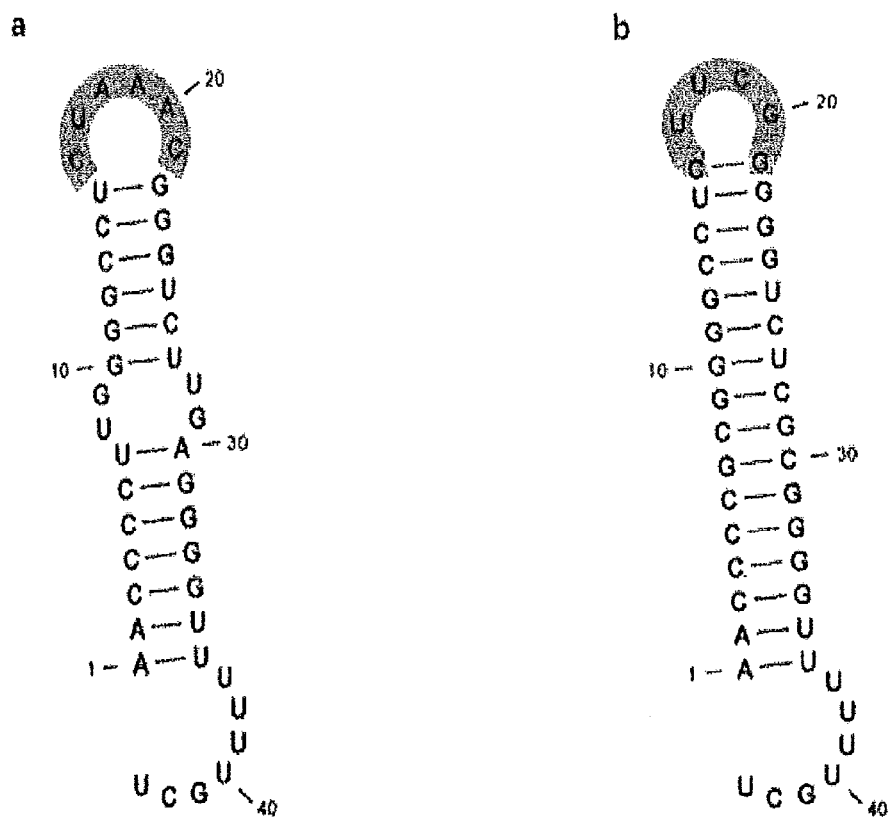
FIG. 4: The artificial terminator "T7UUCG" and the highly similar original T7 terminator hairpin loop. (a) (SEQ ID NO: 38) Wild type T7 terminator contains a loop sequence of six nucleotides and an un-paired region comprising two unpaired G-U residues. (b) (SEQ ID NO: 4) The artificial synthesized novel T7UUCG termination signal exhibit some modifications compared to the original T7 terminator. The hexanucleotide loop is exchanged into the strong nucleation site UUCG. The unpaired region within stem structure is deleted by the presence of G-C base pairs instead of G-U.

Three of those terminators are typical intrinsic terminators. The T7 terminator is the well known hairpin termination signal, also used in the original pET30a. T3 stems from bacteriophage T3 and its structure is similar to that of T7. The third terminator is almost identically to the original T7, but carries some mutations (SEQ ID NO: 4). The primarily hexyloop got exchanged to the extraordinary stable tetraloop UUCG (hence the name "T7UUCG" used herein) and the two weak G-U base pairs within stem structure were exchanged to the more stable G-C base pairs (see FIG. 4).

The original T7 terminator contains more weakly bound G-U base pairs within stem structure, but some of them were described as important interaction sites with T7 polymerase (Schwartz et al., 2003). Surprisingly, increasing A-T and G-C complementarity increased termination efficiency. The last termination signal is a known class II termination signal, originating from vesicular stomatitis virus (VSV). Altogether four novel plasmids, namely Plasmid_V, Plasmid_K, Plasmid_L and Plasmid_M (see Tab. 1) were generated, all containing a second termination signal in addition to the intrinsic plasmid encoded T7 termination signal. To obtain the TE of the four terminators when solely existent, the intrinsic T7 terminator of the original pET30a was deleted (Plasmid_J) and the four inserts were also cloned (SalI/HindIII) into the MCS of the resulting plasmid. Hence four putative plasmids (Plasmid_S, Plasmid_R, Plasmid_Q, and Plasmid_O) were produced (see Tab. 1) and those plasmids just contain a single termination signal at the 3' end of cloned hSOD gene.

All those plasmids in its linearised form were used as templates in an in vitro transcription assay. Purified RNA fractions were analysed with the Bioanalyzer 2100 system in order to calculate termination efficiency. To verify results gained from the used system, Plamid_I with its original termination region containing the T7 terminator was used for in vitro transcription, and subsequent electrophoretic analysis was carried out by using the Bionalyzer system. It turned out that RNA purity is the most important factor influencing the calculated TE. For that purpose insufficiently pure plasmid preparations gained from Wizard Plus SV Minipreps were replaced by more pure plasmid fractions resulting from utilizing QIAfilter Plasmid Midi kit from QIAGEN. As second action an additional purification step using 95% ethanol during RNA precipitation was implemented. Those two steps gained extremely distinct peaks when analysing the RNA transcripts with the Bioanalyzer system. Calculated TE based on those electropherograms revealed a TE of 79.45%±0.35 at the T7 terminator present in Plasmid_I. Hence that value fits well with a TE of 80% for T7 terminator mentioned in literature.

Analyses of the first eight generated plasmids revealed some very interesting and novel features. The individual calculated termination efficiencies are summarised in Tab. 1.

The introduction of a second identical T7 termination signal as accomplished in Plasmid_V does not lead to a remarkable increase of TE. As also described in Jeng et al. (supra) the introduced termination signal just induce a bisection of termination events at the original terminator. The same result could be observed when the highly similar T3 terminator was cloned (Plasmid_K). Surprisingly the simultaneous presence of the artificial termination signal marked T7UUCG and the intrinsic T7 termination signal executed in Plasmid_L dramatically increases total termination efficiency to a value of 93.2%. Thus the adjusted modifications in order to enhance complementarity in the stem triggers a higher TE. Nearly the same effect could be observed with Plasmid_M, which carries a combination of the two different types of Rho-independent termination signals.

As described above the four termination inserts were also cloned into the MCS of Plasmid_J in order to determine the individual TE. At the first view the results (Tab. 1), gained from in vitro transcription utilizing these plasmids as templates, are somewhat surprising. For instance the data reveal that the T7 terminator cloned into the MCS of the shortened plasmid (Plasmid_S) just exhibits a TE of 48.08%, while the same signal in the wild type plasmid (Plasmid_I) shows a calculated TE of nearly 80%. Hence the same terminator possess an extremely different capability to terminate transcription, depending on the actually surrounding sequence. That finding perfectly fits with the observation that the alteration of only few surrounding nucleotides can drastically influence TE of a distinct termination signal. That dependence on encompassing sequences could also explain the difference in calculated TE when a distinct terminator is present in different cloning vectors. Maybe those smaller hairpins aid in termination and are the reason for diminished observed TE in Plasmid_J derivatives. As seen in Tab. 1 all terminators cloned into the MCS of Plasmid_J exhibit a TE below 80%, thus are not as efficient as the original T7 terminator. An explanation might be the presence of further elements in the 104 bp deletion fragment that may influence termination efficiency.

Example 2: Introduction of a Pausing Signal

To further increase termination efficiency the pausing signal T7-CJ was cloned between the two intrinsic terminators of Plasmid_V, Plasmid_K and Plasmid_L. Insert sequences:

TABLE 1

Terminator modified plasmids and their termination efficiency.

| Label | Used plasmid as starting material for cloning | Insert | Cloning site | TE at first terminator | TE at second terminator | TE at intrinsic terminator | TE total (±Stdv) |
|---|---|---|---|---|---|---|---|
| S | pET30a with the deleted intrinsic T7 terminator | hSOD T7 | XbaI/BamHI HindIII/SalI | 48.08% | — | — | 48.08% ± 0.17 |
| R | | hSOD T7UUCG | XbaI/BamHI HindIII/SalI | 67.37% | — | — | 67.37% ± 0.34 |
| Q | | hSOD T3 | XbaI/BamHI HindIII/SalI | 39.45% | — | — | 39.45% ± 0.15 |
| O | | hSOD VSV | XbaI/BamHI HindIII/SalI | 75.87% | — | — | 75.87% ± 0.32 |
| V | pET30 with the intrinsic T7 terminator present | hSOD T7 | XbaI/BamHI HindIII/SalI | 42.68% | | 40.02% | 82.70% ± 0.94 |
| L | | hSOD T7UUCG | XbaI/BamHI HindIII/SalI | 58.28% | — | 34.92% | 93.20% ± 0.02 |
| K | | hSOD T3 | XbaI/BamHI HindIII/SalI | 30.42% | — | 52.25% | 82.69% ± 0.07 |
| M | | hSOD VSV | XbaI/BamHI HindIII/SalI | 65.19% | — | 27.15% | 92.30% ± 0.04 |
| W | pET30 with the intrinsic T7 terminator and the pausing signal CJ-T7 between this original terminator and the cloned one | hSOD T7 CJ-T7 | XbaI/BamHI HindIII/SalI HindIII/NotI | 52.65% | — | 33.22% | 85.87% ± 0.33 |
| Z | | hSOD T7UUCG CJ-T7 | XbaI/BamHI HindIII/SalI HindIII/NotI | 59.03% | — | 28.42% | 87.45% ± 0.09 |
| T | | hSOD T3 CJ-T7 | XbaI/BamHI HindIII/SalI HindIII/NotI | 36.85% | — | 43.56% | 80.41% ± 0.05 |
| ptZENIT | pET30 with the intrinsic T7 terminator present and two additional terminators | hSOD T7UUCG rrnBT1 | XbaI/BamHI HindIII/SalI HindIII/NotI | 59.91% | 32.64% | 6.60% | 98.53% ± 0.03 |
| I | pET30 with the intrinsic T7 terminator present | hSOD | XbaI/BamHI | | | 79.45% | 79.45% ± 0.35 |

```
HindIII_T7-CJ:
                                      (SEQ ID NO: 20)
AGCTTTGTGTCCCTATCTGTTACAGTCTCCTG NotI_T7-CJ:
                                      (SEQ ID NO: 21)
GGCCGCAGGAGACTGTAACAGATAGGGACACAA
```

That pausing signal shares the consensus sequence of all known class II termination signals, but lacks an adjacent run of uridines at the 3' end. It was assumed that a sequence, which forces RNA polymerase to pause, may aid in a more efficient termination because of enlarging the time window within termination can occur. On the one hand the presence of a downstream located pausing signal could lead to a more efficient formation of hairpin structures, by enlarging the time within nucleation of newly synthesised hairpin sequences can occur. Thus hairpin formation gets favoured compared to competitive DNA-RNA hybrid formation. On the other hand a pausing signal in front of a terminator sequence may result in a deceleration of prolonging RNA polymerase, thus could enhance termination. As indicated in Tab. 1, the pausing signal indeed enhances TE at the first terminator, although total termination efficiency is slightly increased in one case (Plasmid_W) and even decreased in the remaining two cases (Plasmid_Z and Plasmid_T) in comparison to terminator combinations without the pausing signal—but still increased in comparison to the native pET30 T7 terminator.

Example 3: Cloning of a Ribosomal Termination Signal

Because of the highest measured TE of the plasmid containing the combination of T7UUCG and T7 this plasmid was taken for further cloning procedures. Terminator 1 (T1) of the enlarged termination region located at the 3' end of the rrnB gene contains both, a class I and class II termination signal. Therefore the insertion of rrnBT1 provides the plasmid with a class II terminator. In addition that ribosomal terminator will enhance secondary structures present at the 3' end. The ribosomal terminator was cloned into the MCS of Plasmid_L directly following the primarily introduced T7UUCG signal. Restriction sites used for cloning were HindIII and NotI. Sequences:

```
NotI_rrnBT1:
                                      (SEQ ID NO: 22)
GGCCGCAGCGACAAACAACAGATAAAACGAAAGGCCCAG-

TCTTTCGACTGAGCCTTTCGTTTTATTTGA

HindIII_rrnBT1:
                                      (SEQ ID NO: 23)
AGCTTCAAATAAAACGAAAGGCTCAGTCGAAA-

GACTGGGCCTTTCGTTTTATCTGTTGTTTGTCGCTGC
```

After generating the modified plasmid, an in vitro transcription assay was carried out, and the transcripts were again separated by using the Bioanalyzer system. As seen in Tab. 1 the additional termination signal again lead to a further increase of total TE (60% TE at the first terminator (T7UUCG), 32% TE at the second terminator (rrnBT1) and 7% TE at the third terminator (native T7)). The calculated overall TE now shows a value of about 98.5%, and reveals this enlarged termination region has a highly efficient transcriptional terminator without overall reduction due to bisecting of the termination reaction. Read through transcripts are dramatically reduced and because of its tremendous potential to stop transcription, this termination signal was named tZENIT, and the pET30a derivative carrying that signal was named ptZENIT.

Example 4: Fed-Batch Cultivation of *E. coli* HMS174(DE3) with Plasmid-J and Plasmid_I to Characterize Effects of T7 Terminator Deletion on Host Cell Response During Full Induction of Recombinant Protein Synthesis As described in example 1.5 pET plasmids with hSOD as model protein were generated with the intrinsic T7 terminator (Plasmid_I) and a 104 bp deletion of the terminator (Plasmid_J). The plasmids were transformed into *E. coli* HMS174(DE3) cells in order to investigate their behaviour during a fermentation process. After one generation in feeding phase cells were fully induced by a high amount of inducer IPTG (20 µmol/g CDM according to the calculated amount of CDM at the end of the process).

Figure 2:
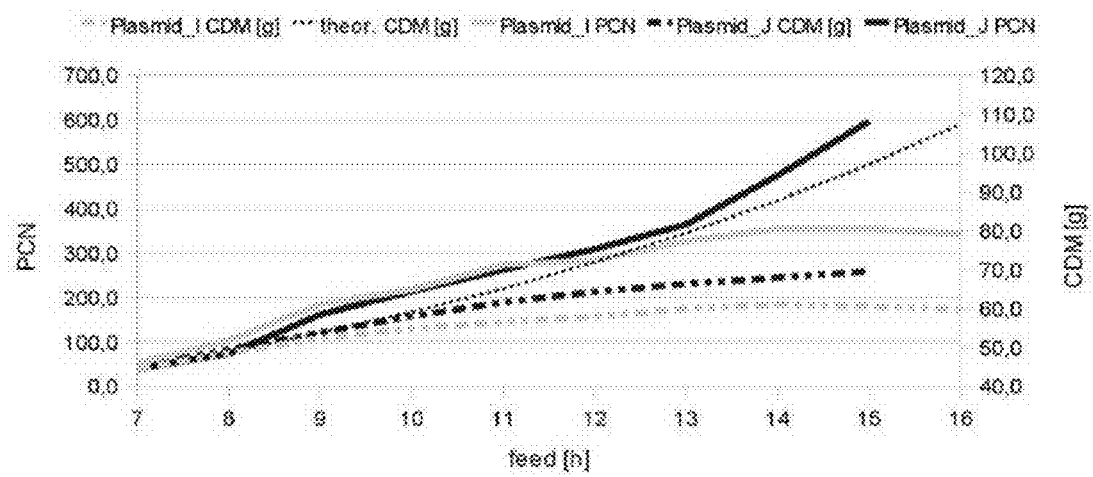
FIG. 2: Fed-batch bioreactor cultivation of *E. coli* HMS174(DE3) strain carrying the modified pET30a plasmids. After one generation (7 h) in feed mode cells were fully induced by adding an inducer amount to achieve an IPTG concentration of 20 μmol/g CDM according to the calculated amount of CDM at the end of the process. Only the first 16 h after feed start are depicted, because after 16 h no cell growth and no putative recombinant protein production could be detected. Plasmid I: intrinsic T7 terminator; Plasmid J: 104 bp deletion of intrinsic T7 terminator. The black line resembles the theoretic cell growth when assuming an exponential growth without limitations. Plasmid J showed increased plasmid copy numbers due to read-throughs but decreased protein (SOD) production.
Figure 2:
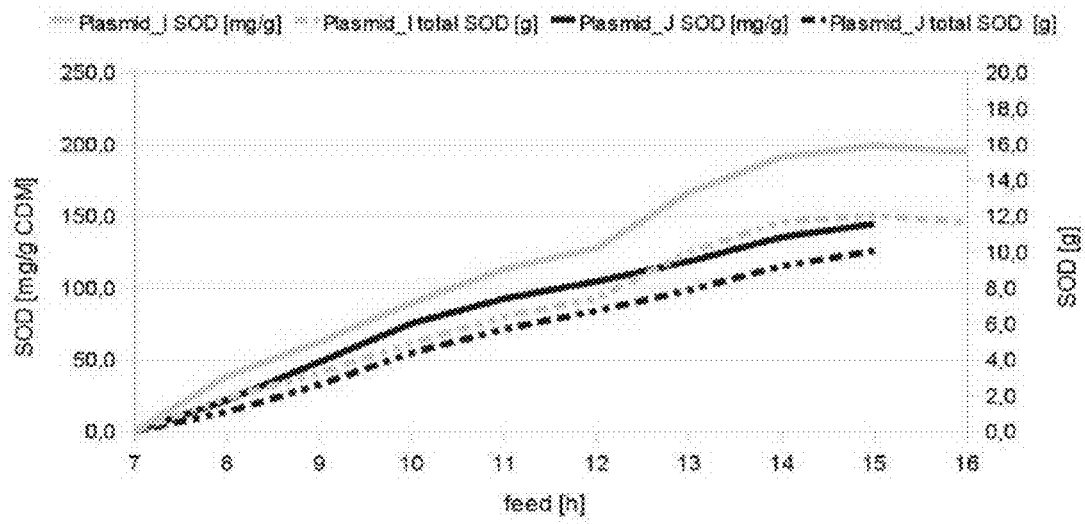

As depicted in FIG. 2 the absence of the transcriptional T7 terminator showed serious effects on host's growth behaviour, on product yield and on plasmid copy number control. Utilizing the wild-type plasmid, the maximal PCN comprises about 350 copies per cell and is reached at feed hour 14 and afterwards PCN gets stabilised at that value. In contrast the absence of a transcriptional terminator dramatically increases the number of plasmids within cells and at feed hour 15 the PCN reaches a value of nearly 600. In accordance to the shape of the PCN curve it could be assumed, that PCN doesn't reach the maximum at feed hour 15, rather PCN will show a further increase. The data clearly reveal, that absence of transcriptional termination strongly interfere with the control of plasmid replication.

Although cells carrying Plasmid_J show a tremendous rise of plasmids per cell, the putative burden to maintain the higher amount of plasmids didn't result in a lowering of growth rate. Rather the strain containing Plasmid_J reaches a higher total cell dry mass (CDM) at the end of the process, and deviation from theoretic biomass growth occurs about one hour later (at 10 h) compared to the strain harbouring Plasmid_I (at 9 h). Thus cell growth phase gets enlarged for 1 h compared to strains carrying the wild-type plasmid. When obtaining the product yield both the specific content of recombinant protein (hSOD/g CDM) as well as the total amount of hSOD (−17%) gets decreased, when the expression vector doesn't comprise a transcriptional terminator. Hence the lack of a termination signal leads to diminished product formation rates, resulting in a lowering of host's metabolic burden and therefore leading to an enlargement of growth phase, which is noticeable in an increase of total CDM. The metabolic burden resulting from plasmid replication in order to maintain the observed increase in PCN seems to be less important, showing little effect on cell growth.

Example 5: Fed-Batch Cultivation of *E. coli* HMS174(DE3) with Carrying the Plasmid ptZENIT to Characterize Effects of tZENIT Terminator on Host Cell Response During Full or Limited Induction of Recombinant Protein Synthesis As described in example 3 the pET30a derivative ptZENIT is characterized by an extremely efficient transcriptional termination region. Under the presumption that insufficient transcriptional termination events have the capability to deregulate plasmid replication, such an enhanced termination should have a noticeable effect on plasmid copy number control. Therefore *E. coli* HMS174(DE3) cells were transformed with plasmid ptZENIT and that production strain was characterized in a bioreactor cultivation process. Recombinant protein production was induced after one generation in feed medium by injecting IPTG (20 μmol/g CDM), thus cells were fully induced.

Figure 5:
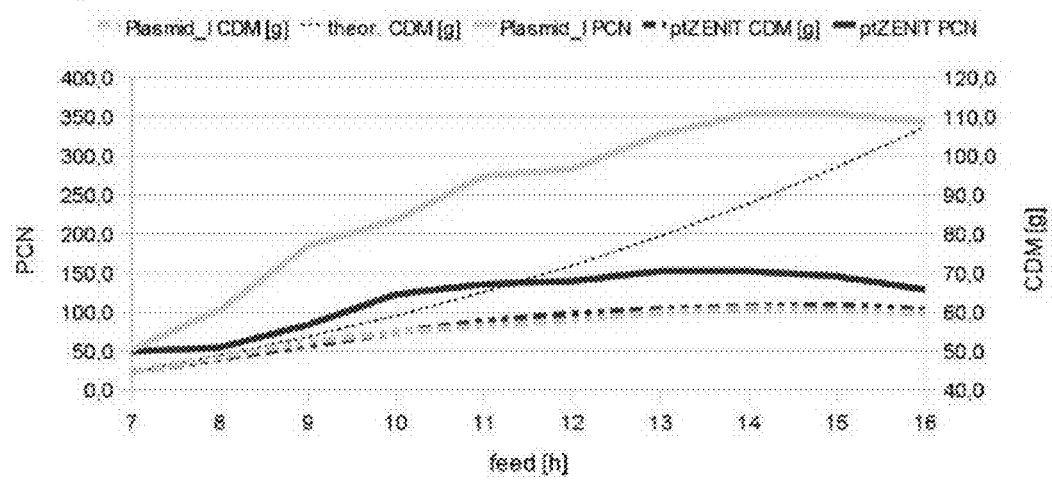
FIG. 5: Fed-batch bioreactor cultivation of *E. coli* HMS174(DE3) strain carrying the indicated pET30a derivatives. After one generation (7 h) in feed mode cells were fully induced by adding an inducer amount to achieve an IPTG concentration of 20 μmol/g CDM according to the calculated amount of CDM at the end of the process. Only the first 16 h after feed start are depicted.
Figure 5:
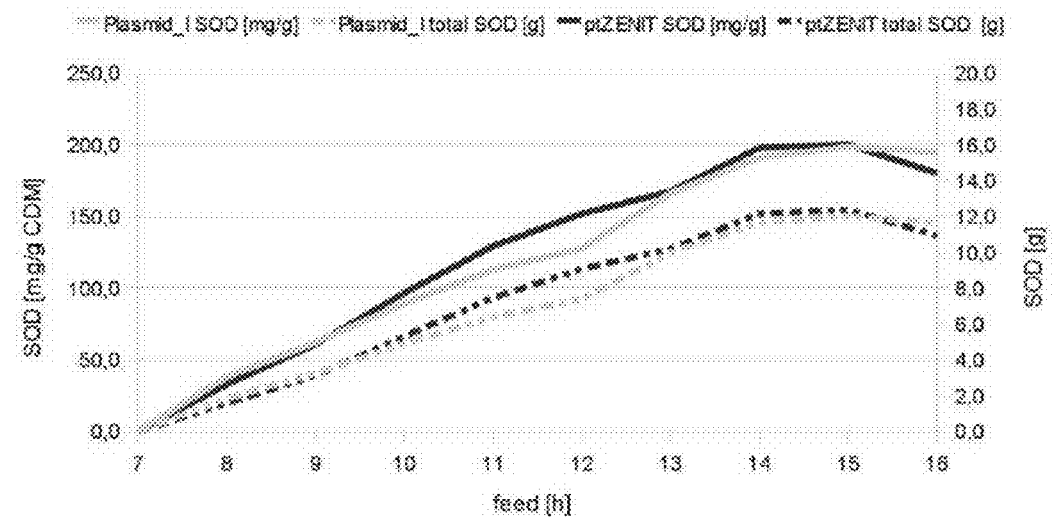

When considering the results given in FIG. 5, it is apparent, that the PCN dramatically decreases from a maximum value of about 350 in reference strain (*E. coli* HMS174 (DE3) with Plasmid_I) to a value of about 150 when harbouring ptZENIT. In both cases those maximal plasmid copy numbers are reached at about feed hour 14 and then are maintained over the whole process. When regarding remaining parameters like total CDM, specific product content and total hSOD amount, no deviations from the ones measured in the reference strain carrying the wild-type plasmid could be detected. The behaviour of *E. coli* HMS174(DE3) strains carrying Plasmid_I or ptZENIT are highly similar when excluding the PCN data. Nevertheless a further evidence for a putative correlation between transcriptional termination and plasmid replication was gained. Under fully induced fermentation conditions the metabolic burden stemming from recombinant protein production seems to be too high, hence reduced energy consumption for maintaining a lower plasmid copy number and the side effect of a reduced gene dosage appear to be of no consequence and do not lead to an enhanced growth of biomass.

Figure 6:
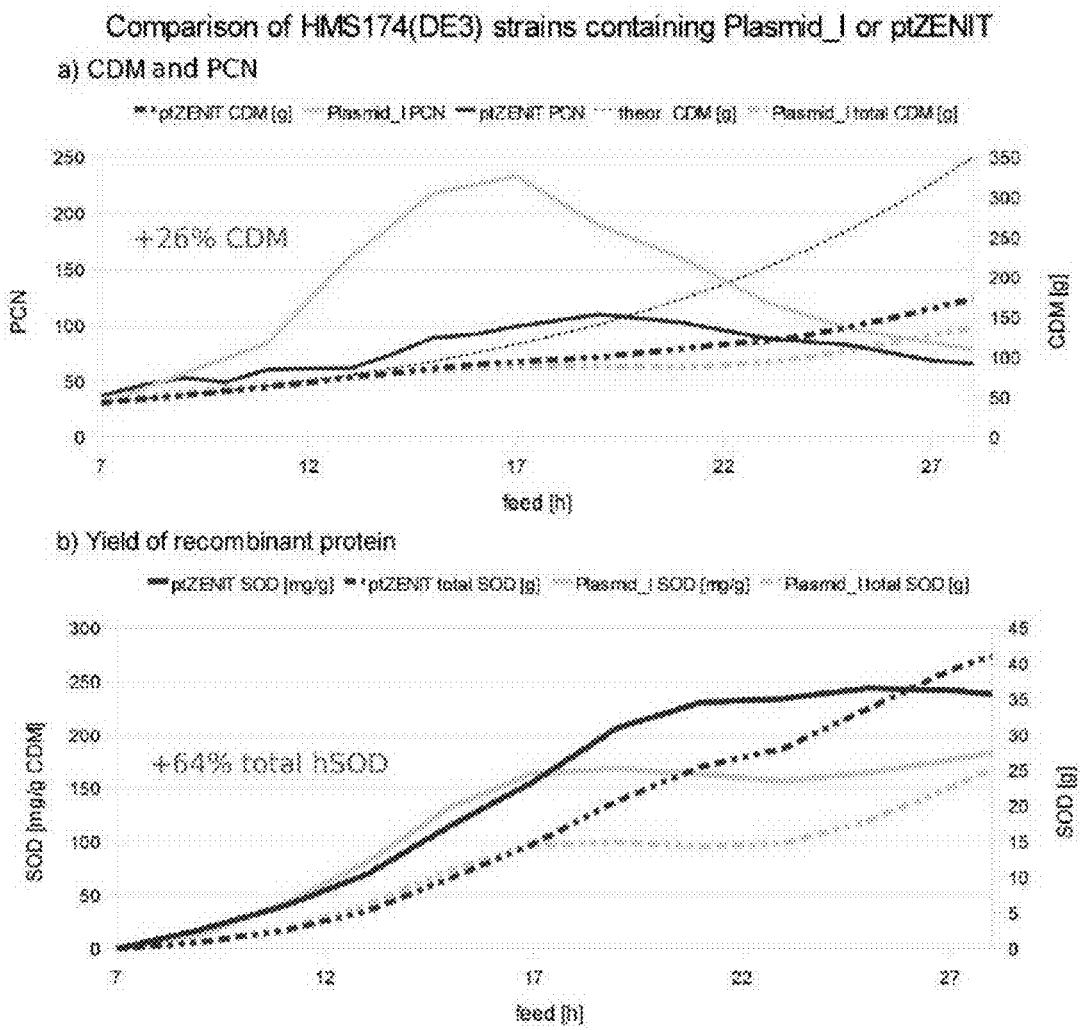
FIG. 6: Fed-batch bioreactor cultivation of *E. coli* HMS174(DE3) strain carrying the indicated pET30a derivatives. After one generation (7 h) in feed mode cells were induced by a continuous inducer feed according to the actually existent CDM (0, 9 μmol/g CDM). Cell growth and recombinant protein production was observed over the whole fermentation process. Cultivation was aborted after 28 h fed batch phase.

To further characterize the consequences on host's viability when carrying ptZENIT as expression vector, a putative bioreactor cultivation was carried out. This time cells were not fully induced, instead the IPTG concentration was maintained under the critical inducer concentration at 0.9 μmol/CDM. As seen in FIG. 6 the more moderate process design drastically increases the viability of host's cells, indicated by a perpetuation of cell growth over the whole process. In comparison to a *E. coli* HMS174(DE3) strain carrying Plasmid_I and cultivated under same conditions, total CDM rises about +26%. That enhanced growth of bacteria cells indicates a lower stress level under production state when using ptZENT as expression vector. As already observed under standard cultivation conditions, again a reduction and stabilisation of PCN was ascertained. When considering the product yield, a remarkable increase of both specific hSOD content and total hSOD could be observed. Specific recombinant protein production rises from a nearly constant value of about 170 mg/g CDM between feed hour 17 h-28 h to a value of about 240 mg/g CDM in case of ptZENIT carrying cells at the same time period. Both the increase in produced biomass as well as the increase of specific hSOD formation escalates total hSOD yield to a value of about +64%. That means, that total yield of hSOD increases from 25 g to a total recovery of about 41 g. Hence the improvement of the transcriptional T7 terminator signal present in the original pET30a plasmid was proved to stabilize plasmid copy number (see FIG. 5 and FIG. 6) and was also shown to possess the capability to positively influence recombinant protein yield.

Example 6: Product Quality

Figure 7:
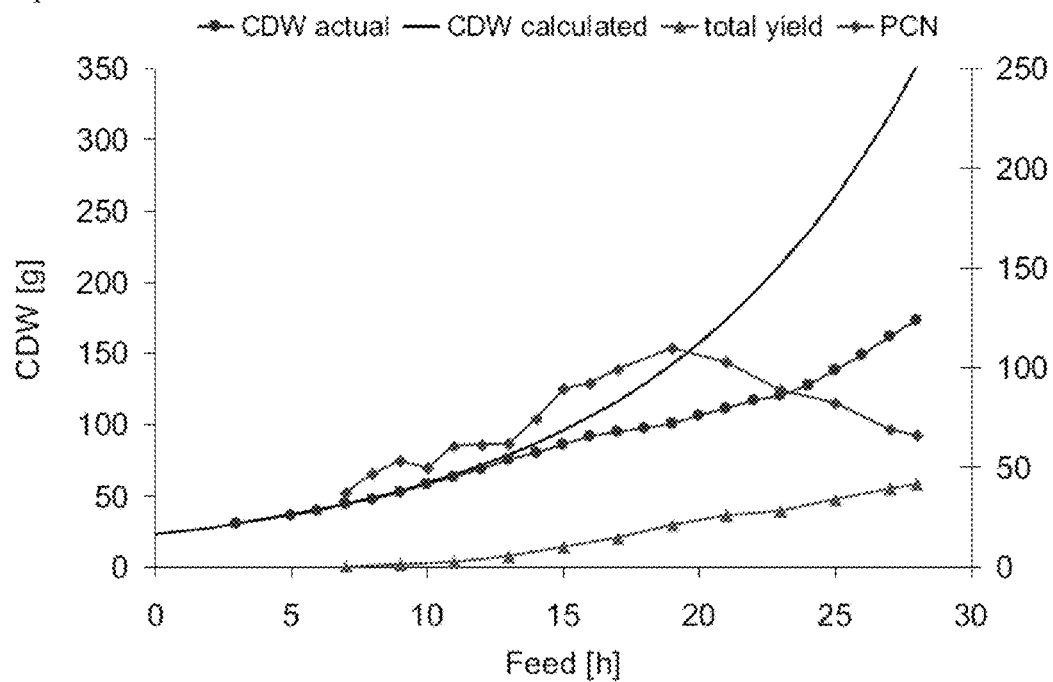
FIG. 7: Fed-batch cultivation with limited induction of *E. coli* HMS174(DE3) (A: ptZENIT, B: pET30a). Course of calculated and actual cell dry weight (CDW), course of plasmid copy number (PCN) and course of total product yield
Figure 7:
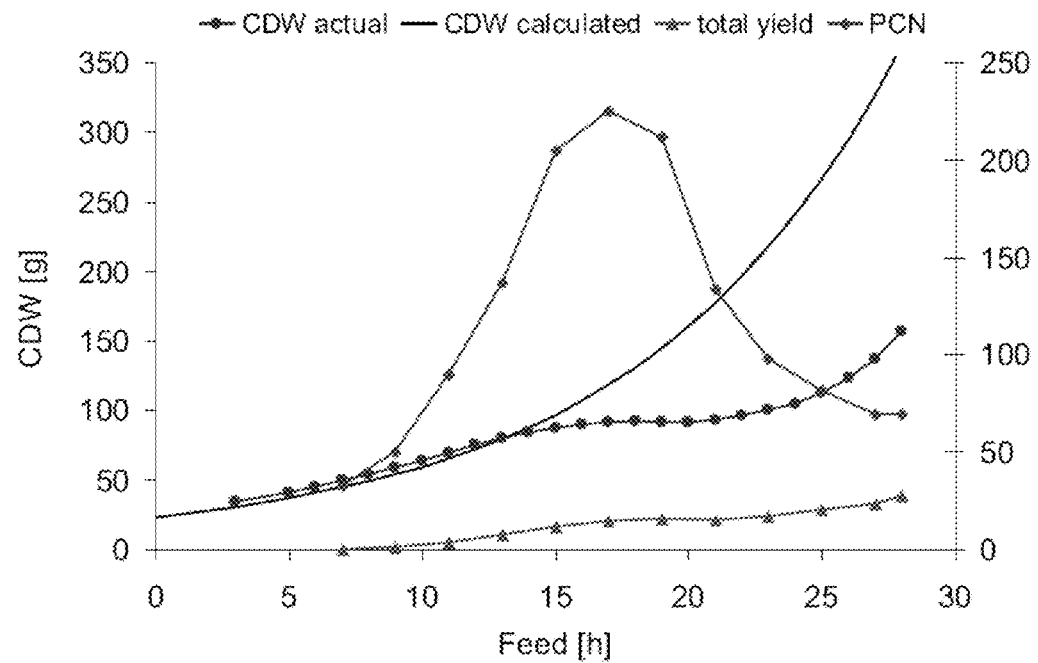
Figure 8:
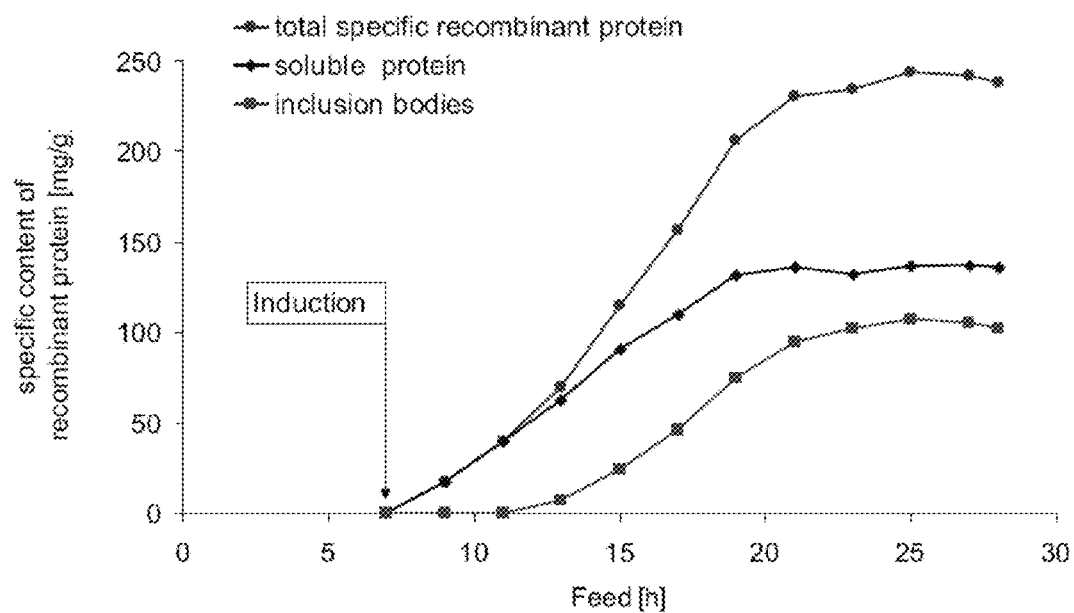
FIG. 8: Fed-batch cultivation with limited induction of *E. coli* HMS174(DE3) (A: ptZENIT, B: pET30a). Courses of soluble, aggregated and total specific recombinant protein (human super oxide dismutase)
Figure 8:
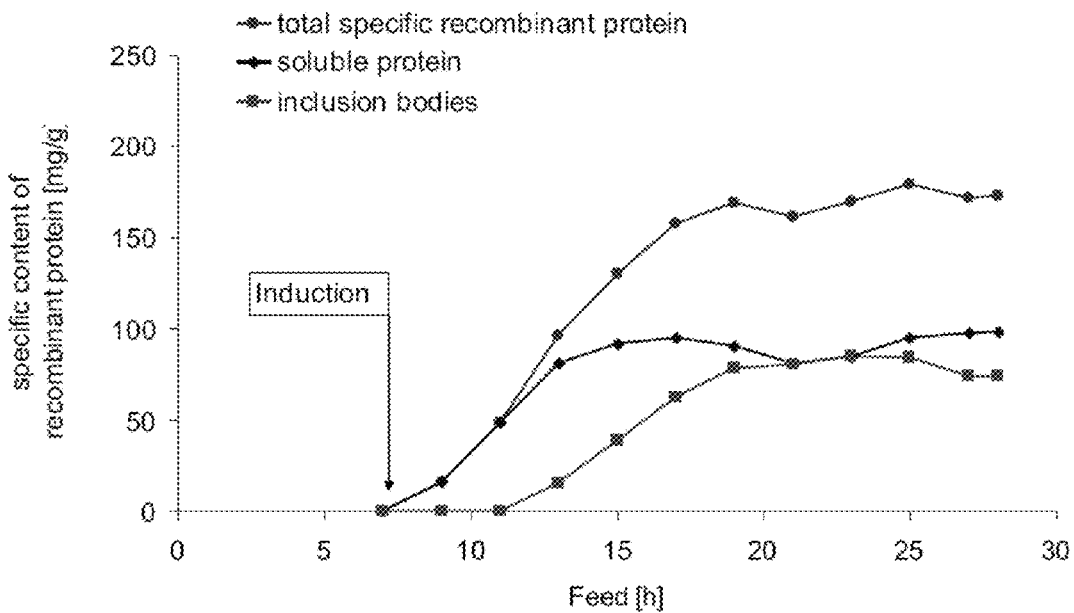
Figure 9:
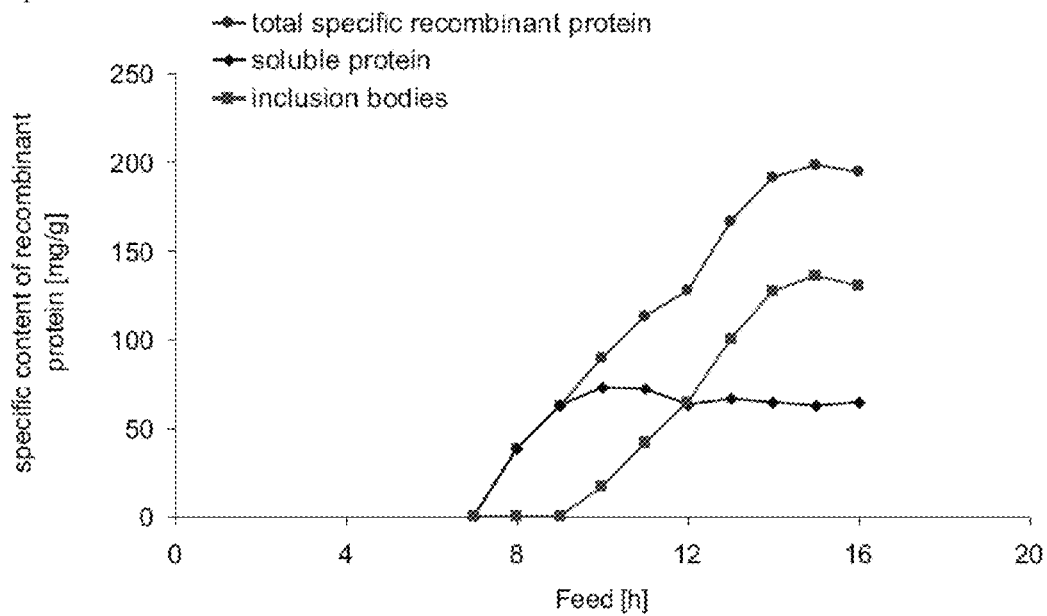
FIG. 9: Fed-batch cultivation with full induction of *E. coli* HMS174(DE3) (A: ptZENIT, B: pET30a). Courses of soluble, aggregated and total specific recombinant protein (human super oxide dismutase)
Figure 9:
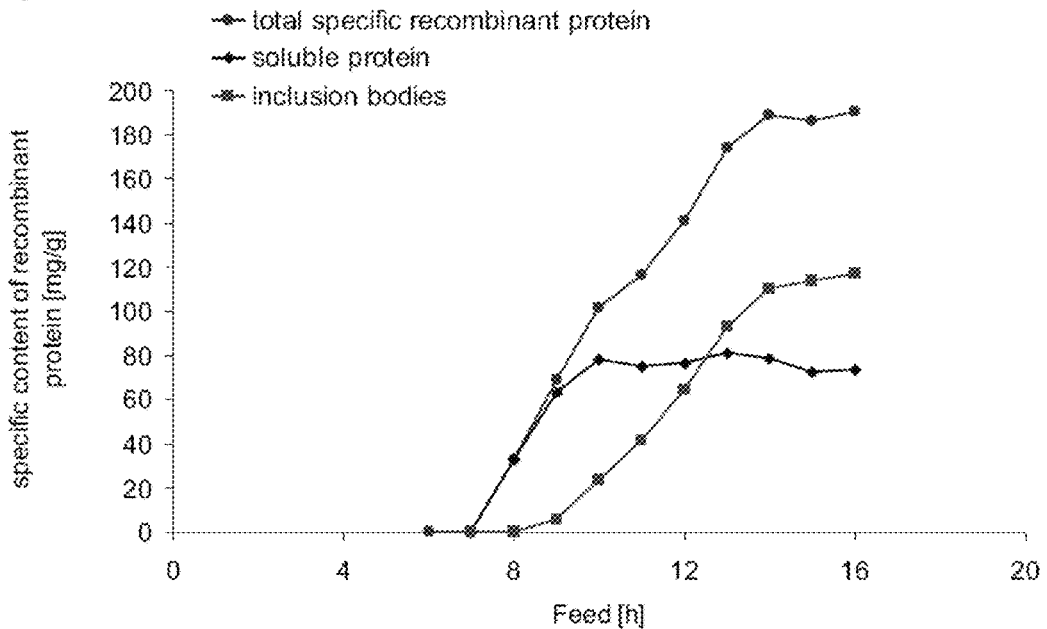

Product quality of recombinant protein (SOD) was investigated during full induction conditions (20 μmol IPTG per g CDM) and limited induction conditions (0.9 μmol IPTG per g CDM). During stress production cells tend to produce incorrectly folded protein leading to aggregates and inclusion bodies. For this invesligation produced SOD was differentiated between soluble SOD and SOD aggregates. Differences between pTZENIT and native pET30a plasmids were demonstrated. As before, plasmid count was lower for pTZENIT, but with increased total protein production (FIG. 7). Types of produced SOD for limited and full induction are shown in FIGS. 8 and 9, respectively. Evidently total production as well as soluble to aggregated SOD was higher for pTZENIT demonstrating increased product quality due to stress-reduced expression conditions through effective termination.

The invention claimed is:

1. An isolated polynucleotide, comprising:
   at least a first and a second transcription termination signal, in any order, that are at most 1000 nucleotides apart, and
   at least one of the transcription termination signals comprises or encodes an RNA hairpin structure, said RNA hairpin structure comprises a stem of least 12 internal base pairs and wherein the RNA hairpin structure is defined by a sequence Y, X, Z, wherein Y is a nucleotide sequence of at least 16 nucleotides in length and with G/C content of at least 75%, X is the sequence U/T-U/T-CG, and Z is a nucleotide sequence with at least 80% complementarity to Y, the complementary nucleotides of Z being base paired with the nucleotides of Y, and X being a loop with no base pairing to Y or Z.

2. The isolated polynucleotide of claim 1, wherein a third transcription termination signal comprises or encodes an RNA hairpin structure, said third transcription termination signal being at most 1000 nucleotides apart from the first or the second transcription termination signal.

3. The isolated polynucleotide of claim 2, wherein the second or third transcription termination signal comprises a RNA hairpin structure and the other of the second or the third transcription termination signal comprises a class II terminator.

4. The isolated polynucleotide of claim 3, wherein the RNA hairpin structure of the second or the third transcription termination signal comprises a wild-type T7 terminator hairpin structure and the class II terminator comprises a T7-CJ pausing signal.

5. The isolated polynucleotide of claim 3, wherein the RNA hairpin structure of the second or the third transcription termination signal comprises a wild-type T7 terminator hairpin structure and the class II terminator comprises a rrnBT1 class II terminator.

6. The isolated polynucleotide of claim 2, wherein the third transcription termination signal comprises or encodes an RNA hairpin structure, said RNA hairpin structure comprises a stem of least 12 internal base pairs and wherein the RNA hairpin structure is defined by a sequence Y, X, Z, wherein Y is a nucleotide sequence of at least 12 nucleotides in length and with G/C content of at least 70%, X is a nucleotide sequence of 4 to 9 nucleotides in length, X comprises or consists of sequence U/T-NNG, with N being any nucleotide selected from U(T), A, C, and G, and Z is a nucleotide sequence with at least 70% complementarity to Y, the complementary nucleotides of Z being base paired with the nucleotides of Y, and X being a loop with no base pairing to Y or Z.

7. The isolated polynucleotide of claim 1, wherein at least one transcription termination signal comprises a A/T(U)-rich region of at least 4 nucleotides in length comprising at least 75% A or T(U).

8. The polynucleotide of claim 7, wherein said A/T(U)-rich region is downstream of a hairpin.

9. The polynucleotide of claim 8, wherein said A/T(U)-rich region is not more than 20 nucleotides apart from said hairpin.

10. The isolated polynucleotide of claim 1, wherein the isolated polynucleotide is DNA.

11. The isolated polynucleotide of claim 1, having a size of at most 10000 nucleotides in length.

12. The isolated polynucleotide of claim 1, wherein the polynucleotide comprises one or more restriction sites flanking said transcription termination signals and/or a cloning site upstream of the transcription termination signals, or a coding sequence upstream of the transcription termination signals.

13. The polynucleotide of claim 12, wherein the coding sequence is operatively linked to a promoter.

14. The isolated polynucleotide of claim 1, comprising:
the first transcription termination signal comprises or encodes an RNA hairpin structure, said RNA hairpin structure comprises a stem of least 14 internal base pairs and wherein the hairpin structure is defined by a sequence Y, X, Z, wherein Y is a nucleotide sequence of at least 16 nucleotides in length and with G/C content of at least 75%, X is the sequence U/T-U/T-CG, and Z is a nucleotide sequence with at least 90% complementarity to Y, the complementary nucleotides of Z being base paired with the nucleotides of Y, and X being a loop with no base pairing to Y or Z; and
the second transcription termination signal comprises or encodes an RNA hairpin structure comprising a sequence Y-X-Z, wherein Y is a nucleotide sequence of at least 8 nucleotides in length and with a G/C content of at least 40%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z,
wherein the first and the second transcription termination signals are at most 1000 nucleotides apart to provide a concerted termination by the first and second termination signals.

15. The polynucleotide of claim 14, wherein Y of the second termination signal has a G/C content of at least 60%.

16. The isolated polynucleotide of claim 1, comprising:
the first transcription termination signal comprises or encodes an RNA hairpin structure, said RNA hairpin structure comprises a stem of least 12 internal base pairs and wherein the RNA hairpin structure is defined by a sequence Y, X, Z, wherein Y is a nucleotide sequence of at least 16 nucleotides in length and with G/C content of at least 75%, X is the sequence U/T-U/T-CG, and Z is a nucleotide sequence with at least 80% complementarity to Y, the complementary nucleotides of Z being base paired with the nucleotides of Y, and X being a loop with no base pairing to Y or Z;
the second transcription termination signal comprises or encodes an RNA hairpin structure, comprising a sequence Y-X-Z, wherein Y is a nucleotide sequence of at least 8 nucleotides in length and with a G/C content of at least 40%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z; and
a third transcription termination signal comprises or encodes an RNA hairpin structure, comprising a sequence Y-X-Z, wherein Y is a nucleotide sequence of at least 8 nucleotides in length and with a G/C content of at least 40%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z;
wherein the first, the second and the third transcription termination signals are at most 1000 nucleotides apart to provide a concerted termination by the first, the second and the third termination signals.

17. The polynucleotide of claim 15, wherein Y of the second and the third termination signals comprise a G/C content of at least 60%.

18. The isolated polynucleotide of claim 1, comprising:
the first transcription termination signal comprises or encodes an RNA hairpin structure, said RNA hairpin structure comprises a stem of least 12 internal base pairs and wherein the RNA hairpin structure is defined by a sequence Y, X, Z, wherein Y is a nucleotide sequence of at least 16 nucleotides in length and with G/C content of at least 75%, X is the sequence U/T-U/T-CG, and Z is a nucleotide sequence with at least 80% complementarity to Y, the complementary nucleotides of Z being base paired with the nucleotides of Y, and X being a loop with no base pairing to Y or Z;
the second transcription termination signal comprises or encodes an RNA hairpin structure comprising a sequence Y-X-Z, wherein Y is a nucleotide sequence of at least 8 nucleotides in length and with a G/C content of at least 40%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z and a class II termination signal adjacent to the hairpin structure comprising the consensus sequence TCTGTT, and having a sequence of at least 20 nucleotides in length with a T content of at least 40%; and
a third transcription termination signal comprises or encodes an RNA hairpin structure comprising a sequence Y-X-Z, wherein Y is a nucleotide sequence of at least 8 nucleotides in length and with a G/C content of at least 40%, X is a nucleotide sequence of 3 to 9 nucleotides in length, and Z is a nucleotide sequence with at least 70% complementarity to Y, the complementary nucleotides of Z being base paired with the nucleotides of Y, and X being a loop with no base pairing to Y or Z;
wherein the first, the second and the third termination signals are at most 1000 nucleotides apart to provide a concerted termination by the first, the second and the third termination signals.

19. The polynucleotide of claim 18, wherein Y of the second and the third termination signals comprise a G/C content of at least 60%.

20. The polynucleotide of claim 1, wherein Y and Z comprise at least 70% G-C, A-T(U) or G-T(U) complementarity.

21. The polynucleotide of claim 1, wherein the second termination signal comprises the consensus sequence TCTGTT.

22. The polynucleotide of claim 1, wherein the second termination signal comprises a sequence of at least 20 nucleotides in length with a T content of at least 40%.

23. The polynucleotide of claim 1, wherein the second termination signal comprises the consensus sequence TCT-GTT.

24. The polynucleotide of claim 1, wherein the second termination signal comprises a sequence of at least 20 nucleotides in length with a T content of at least 40%.

25. The isolated polynucleotide of claim 1, comprising the first transcription termination signal, the second transcription termination signal and a third transcription termination signal,
   wherein at least one of the first and the second transcription termination signals comprises or encodes an RNA hairpin structure, said RNA hairpin structure comprising a stem of least 12 internal base pairs and wherein the RNA hairpin structure is defined by a sequence Y, X, Z, wherein Y is a nucleotide sequence of at least 16 nucleotides in length and with G/C content of at least 75%, X is the sequence U/T-U/T-CG, and Z is a nucleotide sequence with at least 80% complementarity to Y, the complementary nucleotides of Z being base paired with the nucleotides of Y, and X being a loop with no base pairing to Y or Z, and
   said third transcription termination signal comprising or encoding a hairpin structure or class II termination signal at most 1000 nucleotides apart from the first or the second transcription termination signal.

26. The isolated polynucleotide of claim 1, wherein Y is 12-30 nucleotides in length.

27. The isolated polynucleotide of claim 1, wherein Y consists of the nucleotides $y_1$ to $y_m$ and Z consists of the nucleotides $z_1$ to $z_m$, the hairpin consists of the sequence $y_m y_{m-1} y_{m-2} \ldots y_8 y_7 y_6 y_5 y_4 y_3 y_2 y_1$-X-$z_1 z_2 z_3 z_4 z_5 z_6 z_7 z_8 \ldots z_{m-1} z_m$, wherein $z_1$ is complementary to $y_1$, $z_m$ is complementary to $y_m$, and m is an integer from 12 to 30.

28. The isolated polynucleotide of claim 1, wherein Y and Z are at least 90% complementary.

29. The isolated polynucleotide of claim 1, wherein Y and Z are 100% complementary.

30. The isolated polynucleotide of claim 1, wherein, in the hairpin, between nucleotides of Y and Z, at most 3, 2 or 1 G-U complementarities are adjacent to another G-U complementarity.

31. The isolated polynucleotide of claim 1, wherein, in the hairpin, between nucleotides of Y and Z, the hairpin is without adjacent G-U complementarities.

32. The isolated polynucleotide of claim 1, wherein the second transcription termination signal comprises a RNA hairpin structure.

33. The isolated polynucleotide of claim 32, wherein the second transcription termination signal comprises a wild-type T7 terminator hairpin structure.

34. The isolated polynucleotide of claim 1, wherein the second transcription termination signal comprises a class II terminator.

35. An expression cassette comprising a polynucleotide sequence of claim 1, and a coding sequence, wherein the termination signals are operatively positioned for termination of the coding sequence.

36. An isolated vector comprising the polynucleotide of claim 1.

37. An isolated cell comprising a polynucleotide molecule with a gene operatively linked to the transcription termination signals of the polynucleotide of claim 1.

38. The isolated cell of claim 37 said cell comprises a T7 polymerase or a polynucleotide encoding a T7 polymerase.

39. The cell of claim 37, wherein the polynucleotide molecule is in a vector.

40. A method of producing a gene product, comprising providing a cell of claim 37 and cultivating said cell under conditions allowing expression of said gene.

41. An in vitro method of producing a mRNA, comprising providing the polynucleotide of claim 1 and a coding sequence upstream of said transcription termination signal and contacting said polynucleotide with the T7 RNA polymerase.

42. An isolated polynucleotide, comprising or encoding:
   at least one sequence comprising a RNA hairpin structure, wherein the RNA hairpin structure has at least 80% sequence identity to SEQ ID NO: 4, and wherein the RNA hairpin structure comprises a stem of least 12 internal base pairs and wherein the hairpin structure is defined by a sequence Y, X, Z, wherein Y is a nucleotide sequence of at least 16 nucleotides in length and with G/C content of at least 75%, X is a nucleotide sequence of 4 nucleotides in length, X comprises or consists of sequence U/T-NNG, with N being any nucleotide selected from U(T), A, C, G, and Z is a nucleotide sequence with at least 80% complementarity to Y, the complementary nucleotides of Z being base paired with the nucleotides of Y, and X being a loop with no base pairing to Y or Z.

43. The isolated polynucleotide of claim 42, wherein the RNA hairpin has at least 90% sequence identity to SEQ ID NO: 4.

44. The isolated polynucleotide of claim 43, wherein the RNA hairpin has at least 95% sequence identity to SEQ ID NO: 4.

45. The isolated polynucleotide of claim 42, wherein a second sequence comprises a RNA hairpin structure, and wherein the first and the second sequences are at most 1000 nucleotides apart.

46. The isolated polynucleotide of claim 45, wherein the second sequence comprises a wild-type T7 terminator hairpin structure.

47. The isolated polynucleotide of claim 42, wherein a second sequence comprises a class II terminator, and wherein the first and the second sequences are at most 1000 nucleotides apart.

48. The isolated polynucleotide of claim 42, wherein a second or third sequence comprises a RNA hairpin structure and the other of the second or third sequence comprises a class II terminator, and wherein the first and the second sequences are at most 1000 nucleotides apart, and the third sequence is at most 1000 nucleotides apart from the first or the second sequence.

49. The isolated polynucleotide of claim 48, wherein the RNA hairpin structure of the second or the third sequence comprises a wild-type T7 terminator hairpin structure and the class II terminator comprises a T7-CJ pausing signal.

50. The isolated polynucleotide of claim 48, wherein the RNA hairpin structure of the second or the third sequence comprises a wild-type T7 terminator hairpin structure and the class II terminator comprises a rnnBT1 class II terminator.

51. An isolated polynucleotide, comprising:
   at least a first, a second and a third sequence, in any order, that are at most 1000 nucleotides apart, and
   at least one of the first and the second sequences comprises or encodes an RNA hairpin structure, wherein the RNA hairpin has at least 80% sequence identity to SEQ ID NO: 4, and
   said third sequence comprising or encoding a hairpin structure or class II termination signal.

52. The isolated polynucleotide of claim 51, wherein the RNA hairpin has at least 90% sequence identity to SEQ ID NO: 4.

53. The isolated polynucleotide of claim 52, wherein the RNA hairpin has at least 95% sequence identity to SEQ ID NO: 4.

54. The isolated polynucleotide of claim 44, wherein the RNA hairpin is SEQ ID NO: 4.

55. The isolated polynucleotide of claim 53, wherein the RNA hairpin is SEQ ID NO: 4.

* * * * *

SEQUENCE LISTING

```
<160> NUMBER OF SEQ ID NOS: 38

<210> SEQ ID NO 1
<211> LENGTH: 5422
<212> TYPE: DNA
<213> ORGANISM: Artificial Sequence
<220> FEATURE:
<223> OTHER INFORMATION: pET30a Vector Nucleotide Sequence

<400> SEQUENCE: 1
atccggatat  agttcctcct  ttcagcaaaa  aaccectcaa  gacccgttta  gaggccccaa      60
ggggttatgc  tagttattgc  tcagcggtgg  cagcagccaa  ctcagcttcc  tttcgggctt     120
tgttagcagc  cggatctcag  tggtggtggt  ggtggtgctc  gagtgcggcc  gcaagcttgt     180
cgacggagct  cgaattcgga  tccgatatca  gccatggcct  tgtcgtcgtc  gtcggtaccc     240
agatctgggc  tgtccatgtg  ctggcgttcg  aatttagcag  cagcggtttc  tttcatacca     300
gaaccgcgtg  gcaccagacc  agaagaatga  tgatgatgat  ggtgcatatg  tatatctcct     360
tcttaaagtt  aaacaaaatt  atttctagag  gggaattgtt  atccgctcac  aattccccta     420
tagtgagtcg  tattaatttc  gcgggatcga  gatcgatctc  gatcctctac  gccggacgca     480
tcgtggccgg  catcaccggc  gccacaggtg  cggttgctgg  cgcctatatc  gccgacatca     540
```

```
ccgatgggga agatcgggct cgccacttcg ggctcatgag cgcttgtttc ggcgtgggta      600
tggtggcagg ccccgtggcc gggggactgt tgggcgccat ctccttgcat gcaccattcc      660
ttgcggcggc ggtgctcaac ggcctcaacc tactactggg ctgcttccta atgcaggagt      720
cgcataaggg agagcgtcga gatcccggac accatcgaat ggcgcaaaac ctttcgcggt      780
atggcatgat agcgcccgga agagagtcaa ttcagggtgg tgaatgtgaa accagtaacg      840
ttatacgatg tcgcagagta tgccggtgtc tcttatcaga ccgttcccg cgtggtgaac       900 caggccagcc acgtttctgc gaaaacgcgg gaaaagtgg aagcggcgat ggcggagctg       960
aattacattc ccaaccgcgt ggcacaacaa ctggcgggca aacagtcgtt gctgattggc     1020
gttgccacct ccagtctggc cctgcacgcg ccgtcgcaaa ttgtcgcggc gattaaatct     1080
cgcgccgatc aactgggtgc cagcgtggtg gtgtcgatgg tagaacgaag cggcgtcgaa     1140
gcctgtaaag cggcggtgca caatcttctc gcgcaacgcg tcagtgggct gatcattaac     1200
tatccgctgg atgaccagga tgccattgct gtggaagctg cctgcactaa tgttccggcg     1260
ttatttcttg atgtctctga ccagacaccc atcaacagta ttattttctc ccatgaagac     1320
ggtacgcgac tgggcgtgga gcatctggtc gcattgggtc accagcaaat cgcgctgtta     1380
gcgggcccat taagttctgt ctcggcgcgt ctgcgtctgg ctggctggca taaatatctc     1440
actcgcaatc aaattcagcc gatagcggaa cgggaaggcg actggagtgc catgtccggt     1500
tttcaacaaa ccatgcaaat gctgaatgag ggcatcgttc ccactgcgat gctggttgcc     1560
aacgatcaga tggcgctggg cgcaatgcgc gccattaccg agtccgggct gcgcgttggt     1620
gcggacatct cggtagtggg atacgacgat accgaagaca gctcatgtta tcccgccg      1680 ttaaccacca tcaaacagga ttttcgcctg ctggggcaaa ccagcgtgga ccgcttgctg     1740
caactctctc agggccaggc ggtgaagggc aatcagctgt tgcccgtctc actggtgaaa     1800
agaaaaacca ccctggcgcc caatacgcaa accgcctctc ccgcgcgtt ggccgattca      1860 ttaatgcagc tggcacgaca ggtttcccga ctggaaagcg ggcagtgagc gcaacgcaat     1920
taatgtaagt tagctcactc attaggcacc gggatctcga ccgatgccct tgagagcctt     1980
caacccagtc agctccttcc ggtgggcgcg ggcatgact atcgtcgccg cacttatgac      2040
tgtcttcttt atcatgcaac tcgtaggaca ggtgccggca gcgctctggg tcatttttcgg    2100 cgaggaccgg tttcgctgga gcgcgacgat gatcggcctg tcgcttgcgg tattcggaat     2160
cttgcacgcc ctcgctcaag ccttcgtcac tggtcccgcc accaaacgtt tcggcgagaa     2220
gcaggccatt atcgccggca tggcggcccc acgggtgcgc atgatcgtgc tcctgtcgtt     2280
gaggacccgg ctaggctggc ggggttgcct tactggttag cagaatgaat caccgatacg     2340
cgagcgaacg tgaagcgact gctgctgcaa aacgtctgcg acctgagcaa caacatgaat     2400
ggtcttcggt ttccgtgttt cgtaaagtct ggaaacgcgg aagtcagcgc cctgcaccat     2460
tatgttccgg atctgcatcg caggatgctg ctggctaccc tgtggaacac ctacatctgt     2520
attaacgaag cgctggcatt gaccctgagt gatttttctc tggtcccgcc gcatccatac     2580
cgccagttgt ttaccctcac aacgttccag taaccgggca tgttcatcat cagtaacccg     2640
tatcgtgagc atcctctctc gtttcatcgg tatcattacc cccatgaaca gaaatccccc     2700
ttacacggag gcatcagtga ccaaacagga aaaaccgcc cttaacatgg cccgctttat      2760
cagaagccag acattaacgc ttctggagaa actcaacgag ctggacgcgg atgaacaggc     2820
agacatctgt gaatcgcttc acgaccacgc tgatgagctt taccgcagct gcctcgcgcg     2880
tttcggtgat gacggtgaaa acctctgaca catgcagctc ccggagacgg tcacagcttg     2940
```

```
tctgtaagcg gatgccggga gcagacaagc ccgtcagggc gcgtcagcgg gtgttggcgg    3000
gtgtcggggc gcagccatga cccagtcacg tagcgatagc ggagtgtata ctggcttaac    3060
tatgcggcat cagagcagat tgtactgaga gtgcaccata tatgcggtgt gaaataccgc    3120
acagatgcgt aaggagaaaa taccgcatca ggcgctcttc cgcttcctcg ctcactgact    3180
cgctgcgctc ggtcgttcgg ctgcggcgag cggtatcagc tcactcaaag gcggtaatac    3240
ggttatccac agaatcaggg gataacgcag gaaagaacat gtgagcaaaa ggccagcaaa    3300
aggccaggaa ccgtaaaaag gccgcgttgc tggcgttttt ccataggctc cgcccccctg    3360
acgagcatca caaaaatcga cgctcaagtc agaggtggcg aaacccgaca ggactataaa    3420
gataccaggc gtttccccct ggaagctccc tcgtgcgctc tcctgttccg accctgccgc    3480
ttaccggata cctgtccgcc tttctccctt cgggaagcgt ggcgctttct catagctcac    3540
gctgtaggta tctcagttcg gtgtaggtcg ttcgctccaa gctgggctgt gtgcacgaac    3600
cccccgttca gcccgaccgc tgcgccttat ccggtaacta tcgtcttgag tccaacccgg    3660
taagacacga cttatcgcca ctggcagcag ccactggtaa caggattagc agagcgaggt    3720
atgtaggcgg tgctacagag ttcttgaagt ggtggcctaa ctacggctac actagaagga    3780
cagtatttgg tatctgcgct ctgctgaagc cagttacctt cggaaaaaga gttggtagct    3840
cttgatccgg caaacaaacc accgctggta gcggtggttt ttttgtttgc aagcagcaga    3900
ttacgcgcag aaaaaaagga tctcaagaag atcctttgat cttttctacg gggtctgacg    3960
ctcagtggaa cgaaaactca cgttaaggga ttttggtcat gaacaataaa actgtctgct    4020
tacataaaca gtaatacaag gggtgttatg agccatattc aacgggaaac gtcttgctct    4080
aggccgcgat taaattccaa catggatgct gatttatatg ggtataaatg gctcgcgat    4140
aatgtcgggc aatcaggtgc gacaatctat cgattgtatg ggaagcccga tgcgccagag    4200
ttgtttctga acatggcaa aggtagcgtt gccaatgatg ttacagatga atggtcaga    4260
ctaaactggc tgacggaatt tatgcctctt ccgaccatca agcatttat ccgtactcct    4320
gatgatgcat ggttactcac cactgcgatc cccgggaaaa cagcattcca ggtattagaa    4380
gaatatcctg attcaggtga aaatattgtt gatgcgctgg cagtgttcct gcgccggttg    4440
cattcgattc ctgtttgtaa ttgtcctttt aacagcgatc gcgtatttcg tctcgctcag    4500
gcgcaatcac gaatgaataa cggtttggtt gatgcgagtg attttgatga cgagcgtaat    4560
ggctggcctg ttgaacaagt ctggaaagaa atgcataaac ttttgccatt ctcaccggat    4620
tcagtcgtca ctcatggtga tttctcactt gataacctta ttttttgacga ggggaaatta    4680
ataggttgta ttgatgttgg acgagtcgga atcgcagacc gataccagga tcttgccatc    4740
ctatggaact gcctcggtga gttttctcct tcattacaga aacggctttt tcaaaaatat    4800
ggtattgata tcctgatat gaataaattg cagtttcatt tgatgctcga tgagttttc    4860
taagaattaa ttcatgagcg gatacatatt tgaatgtatt tagaaaaata aacaaatagg    4920
ggttccgcgc acatttcccc gaaaagtgcc acctgaaatt gtaaacgtta atattttgtt    4980
aaaattcgcg ttaaattttt gttaaatcag ctcatttttt aaccaatagg ccgaaatcgg    5040
caaaatccct tataaatcaa aagaatagac cgagataggt tgagtgttg ttccagtttg    5100
gaacaagagt ccactattaa agaacgtgga ctccaacgtc aaagggcgaa aaaccgtcta    5160
tcagggcgat ggcccactac gtgaaccatc accctaatca agttttttgg ggtcgaggtg    5220
ccgtaaagca ctaaatcgga acctaaagg gagcccccga tttagagctt gacggggaaa    5280
```

```
gccggcgaac gtggcgagaa aggaagggaa gaaagcgaaa ggagcgggcg ctagggcgct      5340
ggcaagtgta gcggtcacgc tgcgcgtaac caccacaccc gccgcgctta atgcgccgct      5400
acagggcgcg tcccattcgc ca                                              5422
```

<210> SEQ ID NO 2
<211> LENGTH: 5422
<212> TYPE: DNA
<213> ORGANISM: Artificial Sequence
<220> FEATURE:
<223> OTHER INFORMATION: pET30a Vector Reverse Complementary Nucleotide
      Sequence

<400> SEQUENCE: 2

```
tggcgaatgg gacgcgccct gtagcggcgc attaagcgcg gcgggtgtgg tggttacgcg        60
cagcgtgacc gctacacttg ccagcgccct agcgcccgct cctttcgctt tcttcccttc       120
ctttctcgcc acgttcgccg gctttccccg tcaagctcta atcggggggc tccctttagg       180
gttccgattt agtgctttac ggcacctcga ccccaaaaaa cttgattagg gtgatggttc       240
acgtagtggg ccatcgccct gatagacggt ttttcgccct ttgacgttgg agtccacgtt       300
ctttaatagt ggactcttgt tccaaactgg aacaacactc aaccctatct cggtctattc       360
ttttgattta agggatttt gccgatttcg gcctattgg ttaaaaaatg agctgattta         420
acaaaaattt aacgcgaatt ttaacaaaat attaacgttt acaatttcag gtggcacttt        480
tcggggaaat gtgcgcggaa cccctatttg tttatttttc taaatacatt caaatatgta        540
tccgctcatg aattaattct tagaaaaact catcgagcat caaatgaaac tgcaatttat        600
tcatatcagg attatcaata ccatattttt gaaaaagccg tttctgtaat gaaggagaaa        660
actcaccgag gcagttccat aggatggcaa gatcctggta tcggtctgcg attccgactc        720
gtccaacatc aatacaacct attaatttcc cctcgtcaaa aataaggtta tcaagtgaga        780
aatcaccatg agtgacgact gaatccggtg agaatggcaa aagtttatgc atttctttcc        840
agacttgttc aacaggccag ccattacgct cgtcatcaaa atcactcgca tcaaccaaac        900
cgttattcat tcgtgattgc gcctgagcga gacgaaatac gcgatcgctg ttaaaaggac        960
aattacaaac aggaatcgaa tgcaaccggc gcaggaacac tgccagcgca tcaacaatat       1020
tttcacctga tcaggatat tcttctaata cctggaatgc tgttttcccg gggatcgcag        1080
tggtgagtaa ccatgcatca tcaggagtac ggataaaatg cttgatggtc ggaagaggca       1140
taaattccgt cagccagttt agtctgacca tctcatctgt aacatcattg gcaacgctac       1200
ctttgccatg tttcagaaac aactctggcg catcgggctt cccatacaat cgatagattg       1260
tcgcacctga ttgcccgaca ttatcgcgag cccatttata cccatataaa tcagcatcca       1320
tgttggaatt taatcgcggc ctagagcaag acgtttcccg ttgaatatgg ctcataacac       1380
cccttgtatt actgtttatg taagcagaca gttttattgt tcatgaccaa atcccttaa       1440 cgtgagtttt cgttccactg agcgtcagac cccgtagaaa agatcaaagg atcttcttga       1500
gatccttttt ttctgcgcgt aatctgctgc ttgcaaacaa aaaaaccacc gctaccagcg       1560
gtggtttgtt tgccggatca agagctacca actctttttc cgaaggtaac tggcttcagc       1620
agagcgcaga taccaaatac tgtccttcta gtgtagccgt agttaggcca ccacttcaag       1680
aactctgtag caccgcctac atacctcgct ctgctaatcc tgttaccagt ggctgctgcc       1740
agtggcgata gtcgtgtct taccgggttg gactcaagac gatagttacc ggataaggcg       1800
cagcggtcgg gctgaacggg gggttcgtgc acacagccca gcttggagcg aacgacctac       1860
```

```
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccgagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatgtcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
```

```
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc aacagtccc    4800 ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatcga tctcgatccc    4980
gcgaaattaa tacgactcac tatagggaa ttgtgagcgg ataacaattc ccctctagaa    5040
ataattttgt ttaactttaa gaaggagata tacatatgca ccatcatcat catcattctt    5100
ctggtctggt gccacgcggt tctggtatga agaaaccgc tgctgctaaa ttcgaacgcc    5160
agcacatgga cagcccagat ctgggtaccg acgacgacga caaggccatg gctgatatcg    5220
gatccgaatt cgagctccgt cgacaagctt gcggccgcac tcgagcacca ccaccaccac    5280
cactgagatc cggctgctaa caaagcccga aaggaagctg agttggctgc tgccaccgct    5340
gagcaataac tagcataacc ccttggggcc tctaaacggg tcttgagggg ttttttgctg    5400
aaaggaggaa ctatatccgg at                                             5422

<210> SEQ ID NO 3
<211> LENGTH: 73
<212> TYPE: DNA
<213> ORGANISM: Bacteriophage T7

<400> SEQUENCE: 3
aataactagc ataaccccctt ggggcctcta acgggtctt gagggggttttt ttgctgaaag    60 gaggaactat atg                                                         73

<210> SEQ ID NO 4
<211> LENGTH: 43
<212> TYPE: RNA
<213> ORGANISM: Artificial Sequence
<220> FEATURE:
<223> OTHER INFORMATION: optimized terminator sequence

<400> SEQUENCE: 4
aaccccgcgg ggcucuucg ggggucucgc gggguuuuuu gcu                         43

<210> SEQ ID NO 5
<211> LENGTH: 30
<212> TYPE: DNA
<213> ORGANISM: Artificial Sequence
<220> FEATURE:
<223> OTHER INFORMATION: SOD primer

<400> SEQUENCE: 5
gtcgtcggat ccttactatt gggcgatccc                                       30

<210> SEQ ID NO 6
```

```
<211> LENGTH: 28
<212> TYPE: DNA
<213> ORGANISM: Artificial Sequence
<220> FEATURE:
<223> OTHER INFORMATION: SOD primer

<400> SEQUENCE: 6
gtcgtctcta gaaataattt tgtttaac                                         28

<210> SEQ ID NO 7
<211> LENGTH: 24
<212> TYPE: DNA
<213> ORGANISM: Artificial Sequence
<220> FEATURE:
<223> OTHER INFORMATION: T7 deletion primer1

<400> SEQUENCE: 7
ttagcagccg gatctcagtg gtgg                                             24

<210> SEQ ID NO 8
<211> LENGTH: 24
<212> TYPE: DNA
<213> ORGANISM: Artificial Sequence
<220> FEATURE:
<223> OTHER INFORMATION: T7 deletion primer2

<400> SEQUENCE: 8
ggaggaacta tatccggatt ggcg                                             24

<210> SEQ ID NO 9
<211> LENGTH: 26
<212> TYPE: DNA
<213> ORGANISM: Artificial Sequence
<220> FEATURE:
<223> OTHER INFORMATION: class II terminator

<400> SEQUENCE: 9
tgtgtcccta tctgttacag tctcct                                           26

<210> SEQ ID NO 10
<211> LENGTH: 26
<212> TYPE: DNA
<213> ORGANISM: Artificial Sequence
<220> FEATURE:
<223> OTHER INFORMATION: class II terminator

<400> SEQUENCE: 10
atgcttgcca tctgttttct tgcaag                                           26

<210> SEQ ID NO 11
<211> LENGTH: 26
<212> TYPE: DNA
<213> ORGANISM: Artificial Sequence
<220> FEATURE:
<223> OTHER INFORMATION: class II terminator

<400> SEQUENCE: 11
atccatgata tctgttagtt tttttc                                           26

<210> SEQ ID NO 12
<211> LENGTH: 29
<212> TYPE: DNA
<213> ORGANISM: Artificial Sequence
<220> FEATURE:
<223> OTHER INFORMATION: class II terminator

<400> SEQUENCE: 12
```
atccatgata tctgttctcg agtttttt 29

<210> SEQ ID NO 13
<211> LENGTH: 26
<212> TYPE: DNA
<213> ORGANISM: Artificial Sequence
<220> FEATURE:
<223> OTHER INFORMATION: class II terminator

<400> SEQUENCE: 13
tttcgtttta tctgttgttt gtcgtg 26

<210> SEQ ID NO 14
<211> LENGTH: 26
<212> TYPE: DNA
<213> ORGANISM: Artificial Sequence
<220> FEATURE:
<223> OTHER INFORMATION: class II terminator

<400> SEQUENCE: 14
tagttttgta tctgttttgc agcagc 26

<210> SEQ ID NO 15
<211> LENGTH: 26
<212> TYPE: DNA
<213> ORGANISM: Artificial Sequence
<220> FEATURE:
<223> OTHER INFORMATION: class II terminator

<400> SEQUENCE: 15
ttcgaacctc tctgtttact gataag 26

<210> SEQ ID NO 16
<211> LENGTH: 46
<212> TYPE: DNA
<213> ORGANISM: vesicular stomatitis virus

<400> SEQUENCE: 16
tcgacctagc atatccatga tatctgttag tttttttcct gaaaga 46

<210> SEQ ID NO 17
<211> LENGTH: 63
<212> TYPE: DNA
<213> ORGANISM: Bacteriophage T3

<400> SEQUENCE: 17
tcgacctagc ataaacccct tgggttccct ctttaggagt ctgaggggtt ttttgctgaa 60
aga 63

<210> SEQ ID NO 18
<211> LENGTH: 61
<212> TYPE: DNA
<213> ORGANISM: Bacteriophage T7

<400> SEQUENCE: 18
tcgacctagc ataacccctt ggggcctcta aacgggtctt gaggggtttt ttgctgaaag 60
a 61

<210> SEQ ID NO 19
<211> LENGTH: 61
<212> TYPE: DNA
<213> ORGANISM: Artificial Sequence
<220> FEATURE:

<223> OTHER INFORMATION: Optimized Bacteriophage T7 terminator

<400> SEQUENCE: 19

```
tcgacctagc ataaccccgc ggggcctctt cggggtctc gcggggtttt ttgctgaaag    60
a                                                                   61
```

<210> SEQ ID NO 20
<211> LENGTH: 33
<212> TYPE: DNA
<213> ORGANISM: Artificial Sequence
<220> FEATURE:
<223> OTHER INFORMATION: terminator insert

<400> SEQUENCE: 20

```
agctttgtgt ccctatctgt tacagtctcc tgc                                33
```

<210> SEQ ID NO 21
<211> LENGTH: 33
<212> TYPE: DNA
<213> ORGANISM: Artificial Sequence
<220> FEATURE:
<223> OTHER INFORMATION: terminator insert

<400> SEQUENCE: 21

```
ggccgcagga gactgtaaca gatagggaca caa                                33
```

<210> SEQ ID NO 22
<211> LENGTH: 69
<212> TYPE: DNA
<213> ORGANISM: Artificial Sequence
<220> FEATURE:
<223> OTHER INFORMATION: terminator insert

<400> SEQUENCE: 22

```
ggccgcagcg acaaacaaca gataaaacga aaggcccagt ctttcgactg agcctttcgt    60
tttatttga                                                           69
```

<210> SEQ ID NO 23
<211> LENGTH: 69
<212> TYPE: DNA
<213> ORGANISM: Artificial Sequence
<220> FEATURE:
<223> OTHER INFORMATION: terminator insert

<400> SEQUENCE: 23

```
agcttcaaat aaaacgaaag gctcagtcga agactgggcc tttcgtttt atctgttgtt    60
tgtcgctgc                                                           69
```

<210> SEQ ID NO 24
<211> LENGTH: 105
<212> TYPE: DNA
<213> ORGANISM: Artificial Sequence
<220> FEATURE:
<223> OTHER INFORMATION: Synthetic

<400> SEQUENCE: 24

```
agatcgatct cgatcccgcg aaattaatac gactcactat aggggaattg tgagcggata    60
acaattcccc tctagaaata attttgttta actttaagaa ggaga                  105
```

<210> SEQ ID NO 25
<211> LENGTH: 115
<212> TYPE: DNA
<213> ORGANISM: Artificial Sequence

```
<220> FEATURE:
<223> OTHER INFORMATION: Synthetic

<400> SEQUENCE: 25
tatacatatg caccatcatc atcatcattc ttctggtctg gtgccacgcg gttctggtat    60
gaaagaaacc gctgctgcta aattcgaacg ccagcacatg gacagcccag atctg        115

<210> SEQ ID NO 26
<211> LENGTH: 36
<212> TYPE: PRT
<213> ORGANISM: Artificial Sequence
<220> FEATURE:
<223> OTHER INFORMATION: Synthetic

<400> SEQUENCE: 26

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu
        35

<210> SEQ ID NO 27
<211> LENGTH: 117
<212> TYPE: DNA
<213> ORGANISM: Artificial Sequence
<220> FEATURE:
<223> OTHER INFORMATION: Synthetic

<400> SEQUENCE: 27
ggtaccgacg acgacgacaa ggccatggct gatatcggat ccgaattcga gctccgtcga    60
caagcttgcg gccgcactcg agcaccacca ccaccaccac tgagatccgg ctgctaa      117

<210> SEQ ID NO 28
<211> LENGTH: 38
<212> TYPE: PRT
<213> ORGANISM: Artificial Sequence
<220> FEATURE:
<223> OTHER INFORMATION: Synthetic

<400> SEQUENCE: 28

Gly Thr Asp Asp Asp Asp Lys Ala Met Ala Asp Ile Gly Ser Glu Phe
1               5                   10                  15

Glu Leu Arg Arg Gln Ala Cys Gly Arg Thr Arg Ala Pro Pro Pro Pro
            20                  25                  30

Pro Leu Arg Ser Gly Cys
        35

<210> SEQ ID NO 29
<211> LENGTH: 75
<212> TYPE: DNA
<213> ORGANISM: Artificial Sequence
<220> FEATURE:
<223> OTHER INFORMATION: Synthetic

<400> SEQUENCE: 29
gcgatatcgg atccgaattc gagctccgtc gacaagcttg cggccgcact cgagcaccac    60
caccaccacc actga                                                    75

<210> SEQ ID NO 30
<211> LENGTH: 24
<212> TYPE: PRT
```

<213> ORGANISM: Artificial Sequence
<220> FEATURE:
<223> OTHER INFORMATION: Synthetic

<400> SEQUENCE: 30

Ala Ile Ser Asp Pro Asn Ser Ser Val Asp Lys Leu Ala Ala Ala
1               5                   10                  15

Leu Glu His His His His His His
            20

<210> SEQ ID NO 31
<211> LENGTH: 91
<212> TYPE: DNA
<213> ORGANISM: Artificial Sequence
<220> FEATURE:
<223> OTHER INFORMATION: Synthetic

<400> SEQUENCE: 31
ggatatctgt ggatccgaat tcgagctccg tcgacaagct tgcggccgca ctcgagcacc    60
accaccacca ccactgagat ccggctgcta a                                  91

<210> SEQ ID NO 32
<211> LENGTH: 30
<212> TYPE: PRT
<213> ORGANISM: Artificial Sequence
<220> FEATURE:
<223> OTHER INFORMATION: Synthetic

<400> SEQUENCE: 32

Gly Tyr Leu Trp Ile Arg Ile Arg Ala Pro Ser Thr Ser Leu Arg Pro
1               5                   10                  15

His Ser Ser Thr Thr Thr Thr Thr Thr Glu Ile Arg Leu Leu
            20                  25                  30

<210> SEQ ID NO 33
<211> LENGTH: 97
<212> TYPE: DNA
<213> ORGANISM: Artificial Sequence
<220> FEATURE:
<223> OTHER INFORMATION: Synthetic

<400> SEQUENCE: 33
caaagcccga aaggaagctg agttggctgc tgccaccgct gagcaataac tagcataacc    60
ccttggggcc tctaaacggg tcttgagggg tttttg                             97

<210> SEQ ID NO 34
<211> LENGTH: 69
<212> TYPE: DNA
<213> ORGANISM: Artificial Sequence
<220> FEATURE:
<223> OTHER INFORMATION: Synthetic

<400> SEQUENCE: 34
gtcgacctag cataaacccc ttgggttccc tctttaggag tctgaggggt ttttgctga    60 aagaagctt                                                          69

<210> SEQ ID NO 35
<211> LENGTH: 67
<212> TYPE: DNA
<213> ORGANISM: Artificial Sequence
<220> FEATURE:
<223> OTHER INFORMATION: Synthetic

<400> SEQUENCE: 35

```
gtcgacctag cataacccct tggggcctct aaacgggtct tgagggtttt tttgctgaaa      60
gaagctt                                                                67

<210> SEQ ID NO 36
<211> LENGTH: 67
<212> TYPE: DNA
<213> ORGANISM: Artificial Sequence
<220> FEATURE:
<223> OTHER INFORMATION: Synthetic

<400> SEQUENCE: 36
gtcgacctag cataaccccg cggggcctct tcggggtct cgcggggttt tttgctgaaa       60
gaagctt                                                                67

<210> SEQ ID NO 37
<211> LENGTH: 52
<212> TYPE: DNA
<213> ORGANISM: Artificial Sequence
<220> FEATURE:
<223> OTHER INFORMATION: Synthetic

<400> SEQUENCE: 37
gtcgacctag catatccatg atatctgtta gttttttcc tgaaagaagc tt               52

<210> SEQ ID NO 38
<211> LENGTH: 43
<212> TYPE: RNA
<213> ORGANISM: Artificial Sequence
<220> FEATURE:
<223> OTHER INFORMATION: Synthetic

<400> SEQUENCE: 38
aaccccuugg ggccuguaaa cgggucuuga gggguuuuuu gcu                        43
```